United States Patent
Allred et al.

(10) Patent No.: US 7,059,857 B2
(45) Date of Patent: *Jun. 13, 2006

(54) SUBSTANTIALLY SOLID DESENSITIZING COMPOSITIONS AND DEVICES HAVING A TRAY-LIKE CONFIGURATION AND METHODS OF MANUFACTURING AND USING SUCH COMPOSITIONS AND DEVICES

(75) Inventors: Peter M. Allred, Riverton, UT (US); Neil T. Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 389 days.

This patent is subject to a terminal disclaimer.

(21) Appl. No.: 10/637,237

(22) Filed: Aug. 8, 2003

(65) Prior Publication Data

US 2004/0241617 A1 Dec. 2, 2004

Related U.S. Application Data

(63) Continuation-in-part of application No. 10/446,235, filed on May 27, 2003, and a continuation-in-part of application No. 10/446,741, filed on May 27, 2003.

(51) Int. Cl.
*A61C 15/00* (2006.01)
*A61K 9/20* (2006.01)

(52) U.S. Cl. ............... 433/216; 424/53; 433/215
(58) Field of Classification Search ........... 433/80, 433/215; 424/53; 206/63.5, 369
See application file for complete search history.

(56) References Cited

U.S. PATENT DOCUMENTS

| 165,584 A | 7/1875 | Hopfen |
| 1,637,153 A | 7/1927 | Lawton |
| 2,257,709 A | 9/1941 | Anderson ............ 128/260 |
| 2,835,628 A | 5/1958 | Saffir ............ 167/84 |
| 3,339,547 A | 9/1967 | Drabkowski ............ 128/260 |
| 3,527,219 A | 9/1970 | Greenberg ............ 128/260 |
| 3,577,640 A | 5/1971 | Lee ............ 32/32 |

(Continued)

FOREIGN PATENT DOCUMENTS

WO   WO 88/06869   9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).

*Primary Examiner*—Todd E. Manahan
(74) *Attorney, Agent, or Firm*—Workman Nydegger

(57) ABSTRACT

Dental desensitizing compositions are in the shape of a dental tray or tray-like configuration, optionally in combination with a protective barrier layer. Shaped desensitizing compositions comprise a substantially solid dental desensitizing composition that has increased adhesiveness to teeth when moistened with saliva or water. The shape of the dental desensitizing composition facilitates placement of the composition over a person's teeth with substantially less manipulation compared to the use of initially flat strips. The substantially solid dental desensitizing composition becomes more adhesive when moistened with saliva or water, yet remains intact and coherent after the dental desensitizing composition is placed over a person's teeth during desensitizing, particularly when used in combination with a moisture-resistant barrier. The result is that the moistened dental desensitizing composition is able to reliably adhere against a user's teeth during a desensitizing procedure.

60 Claims, 7 Drawing Sheets

U.S. PATENT DOCUMENTS

| | | | |
|---|---|---|---|
| 3,624,909 A | 12/1971 | Greenberg | 32/40 |
| 3,688,406 A | 9/1972 | Porter et al. | 32/40 R |
| 3,955,281 A | 5/1976 | Weitzman | 32/14 B |
| 4,044,762 A | 8/1977 | Jacobs | 128/136 |
| 4,063,552 A | 12/1977 | Going et al. | 128/136 |
| 4,064,628 A | 12/1977 | Weitzman | 32/14 B |
| 4,138,814 A | 2/1979 | Weitzman | 32/14 B |
| RE33,093 E | 10/1989 | Schiraldi et al. | 424/676 |
| 4,900,721 A | 2/1990 | Bansemir | |
| 4,902,227 A | 2/1990 | Smith | 433/215 |
| 5,008,093 A | 4/1991 | Merianos | |
| 5,051,476 A | 9/1991 | Uji et al. | 525/186 |
| 5,085,585 A | 2/1992 | Zimble | 433/80 |
| 5,108,742 A | 4/1992 | Merianos | |
| 5,112,225 A | 5/1992 | Diesso | 433/48 |
| 5,183,901 A | 2/1993 | Login et al. | |
| 5,211,559 A | 5/1993 | Hart et al. | 433/80 |
| 5,310,563 A | 5/1994 | Curtis et al. | 424/616 |
| 5,326,685 A | 7/1994 | Gaglio et al. | 433/215 |
| 5,346,061 A | 9/1994 | Newman et al. | 206/221 |
| 5,356,291 A | 10/1994 | Darnell | 433/216 |
| 5,376,006 A | 12/1994 | Fischer | 433/215 |
| 5,425,953 A | 6/1995 | Sintov et al. | 424/404 |
| 5,562,449 A | 10/1996 | Jacobs et al. | 433/215 |
| 5,573,399 A | 11/1996 | McClintock, II | 433/80 |
| 5,575,654 A | 11/1996 | Fontenot | 433/215 |
| 5,611,687 A | 3/1997 | Wagner | 433/80 |
| 5,616,027 A | 4/1997 | Jacobs et al. | 433/37 |
| 5,631,000 A | 5/1997 | Pellico | 424/53 |
| 5,639,445 A | 6/1997 | Curtis et al. | 424/49 |
| 5,702,251 A | 12/1997 | McClintock, II | 433/80 |
| 5,707,235 A | 1/1998 | Knutson | 433/213 |
| 5,711,935 A | 1/1998 | Hill et al. | 424/49 |
| 5,752,826 A | 5/1998 | Andreiko | 433/41 |
| 5,769,633 A | 6/1998 | Jacobs et al. | 433/37 |
| 5,816,802 A | 10/1998 | Montgomery | 433/80 |
| 5,846,058 A | 12/1998 | Fischer | 433/216 |
| 5,851,512 A | 12/1998 | Fischer | 424/49 |
| 5,863,202 A | 1/1999 | Fontenot et al. | 433/215 |
| 5,879,691 A | 3/1999 | Sagel et al. | 429/401 |
| 5,891,453 A | 4/1999 | Sagel et al. | 424/401 |
| 5,894,017 A | 4/1999 | Sagel et al. | 424/401 |
| 5,895,218 A | 4/1999 | Quinn et al. | 433/80 |
| 5,922,307 A | 7/1999 | Montgomery | 424/53 |
| 5,924,863 A | 7/1999 | Jacobs et al. | 433/80 |
| 5,980,249 A | 11/1999 | Fontenot | 433/80 |
| 5,985,249 A | 11/1999 | Fischer | 424/49 |
| 5,989,569 A | 11/1999 | Dirksing et al. | 424/401 |
| 6,045,811 A | 4/2000 | Dirksing et al. | 424/401 |
| 6,080,397 A | 6/2000 | Pfirrmann | |
| 6,089,869 A | 7/2000 | Schwartz | 433/215 |
| 6,096,328 A | 8/2000 | Sagel et al. | 424/401 |
| 6,106,293 A | 8/2000 | Wiesel | 433/215 |
| 6,126,443 A | 10/2000 | Burgio | 433/215 |
| 6,136,297 A | 10/2000 | Sagel et al. | 424/49 |
| 6,142,780 A | 11/2000 | Burgio | 433/80 |
| 6,155,832 A | 12/2000 | Wiesel | 433/215 |
| 6,183,251 B1 | 2/2001 | Fischer | 433/48 |
| 6,197,331 B1 | 3/2001 | Lerner et al. | 424/448 |
| 6,247,930 B1 | 6/2001 | Chiang et al. | 433/80 |
| 6,274,122 B1 | 8/2001 | McLaughlin | 424/53 |
| 6,277,458 B1 | 8/2001 | Dirksing et al. | 424/42.3 |
| 6,280,196 B1 | 8/2001 | Berghash | 433/215 |
| 6,287,120 B1 | 9/2001 | Wiesel | 433/215 |
| 6,309,625 B1 | 10/2001 | Jensen et al. | 424/49 |
| 6,312,671 B1 | 11/2001 | Jensen et al. | 424/53 |
| 6,322,360 B1 | 11/2001 | Burgio | 433/80 |
| 6,331,292 B1 | 12/2001 | Montgomery | 424/53 |
| 6,343,932 B1 | 2/2002 | Wiesel | 433/215 |
| 6,364,665 B1 | 4/2002 | Trettemerp | 433/215 |
| 6,379,147 B1 | 4/2002 | Georgakis et al. | 433/37 |
| 6,419,903 B1 | 7/2002 | Xu et al. | 424/49 |
| 6,419,906 B1 | 7/2002 | Xu et al. | 424/53 |
| 6,435,873 B1 | 8/2002 | Burgio | 433/80 |
| 6,440,396 B1 | 8/2002 | McLaughlin | 424/49 |
| 6,458,380 B1 | 10/2002 | Leaderman | 424/443 |
| 6,461,158 B1 | 10/2002 | Sagel et al. | 433/30 |
| 6,488,914 B1 | 12/2002 | Montgomery | 424/53 |
| 6,497,575 B1 | 12/2002 | Zavitsanos et al. | 433/215 |
| 6,500,408 B1 | 12/2002 | Chen | 424/53 |
| 6,503,486 B1 | 1/2003 | Xu et al. | 424/53 |
| 6,506,053 B1 | 1/2003 | Wiesel | 433/215 |
| 6,514,483 B1 | 2/2003 | Xu et al. | 424/53 |
| 6,514,484 B1 | 2/2003 | Rajaiah et al. | 424/53 |
| 6,551,579 B1 | 4/2003 | Sagel et al. | 424/53 |
| 6,649,147 B1 | 11/2003 | Ye et al. | |
| 6,682,721 B1 | 1/2004 | Kim et al. | |
| 6,689,344 B1 | 2/2004 | Chang et al. | |
| 6,730,316 B1 | 5/2004 | Chen | |
| 2001/0046654 A1 | 11/2001 | Zavitsanos et al. | 433/32 |
| 2002/0006387 A1 | 1/2002 | Sagel et al. | 424/53 |
| 2002/0006388 A1 | 1/2002 | Sagel et al. | 424/53 |
| 2002/0012685 A1 | 1/2002 | Sagel et al. | 424/401 |
| 2002/0018754 A1 | 2/2002 | Sagel et al. | 424/49 |
| 2002/0081555 A1 | 6/2002 | Wiesel | 433/215 |
| 2002/0164292 A1 | 11/2002 | Peterson et al. | 424/53 |
| 2002/0182154 A1 | 12/2002 | McLaughlin | 424/53 |
| 2002/0187111 A1 | 12/2002 | Xu et al. | 424/53 |
| 2002/0187112 A1 | 12/2002 | Xu et al. | 424/53 |
| 2003/0003421 A1 | 1/2003 | Besenheider et al. | 433/215 |
| 2003/0012747 A1 | 1/2003 | Peterson | 424/53 |
| 2003/0036037 A1 | 2/2003 | Zavitsanos et al. | 433/215 |
| 2003/0044631 A1 | 3/2003 | Sagal et al. | 428/548 |
| 2003/0068284 A1 | 4/2003 | Sagel et al. | 424/53 |
| 2003/0068601 A1 | 4/2003 | Zavitsanos et al. | 433/215 |
| 2003/0082114 A1 | 5/2003 | Kim et al. | 424/53 |
| 2003/0133884 A1 | 7/2003 | Chang et al. | 424/53 |
| 2003/0194382 A1 | 10/2003 | Chang et al. | 424/53 |
| 2003/0198606 A1 | 10/2003 | Kim et al. | 424/53 |
| 2004/0005277 A1 * | 1/2004 | Willison et al. | 424/53 |

FOREIGN PATENT DOCUMENTS

WO      WO 03/000216      1/2003

* cited by examiner

SUBSTANTIALLY SOLID DESENSITIZING COMPOSITIONS AND DEVICES HAVING A TRAY-LIKE CONFIGURATION AND METHODS OF MANUFACTURING AND USING SUCH COMPOSITIONS AND DEVICES

CROSS-REFERENCE TO RELATED APPLICATIONS

This application is a continuation-in-part of copending U.S. application Ser. No. 10/446,235, filed May 27, 2003, and a continuation-in-part of copending U.S. application Ser. No. 10/446,471, filed May 27, 2003. The foregoing applications are incorporated by reference in their entirely.

BACKGROUND OF THE INVENTION

1. The Field of the Invention

The present invention is in the field of dental desensitizing compositions used to desensitize a person's teeth. More particularly, the invention relates to substantially solid dental desensitizing compositions and devices in the shape of a dental tray that becomes adhesive when moistened (e.g., by saliva on a user's teeth), as well as methods for their manufacture and use.

2. The Relevant Technology

Tooth sensitivity is a common problem for many dental patients. This sensitivity may result from or be associated with the existence of a cavity, tooth or root fractures, gingival recession, exposed dentin, toothbrush abrasion, bleaching, attrition, erosion, grinding, or trauma from periodontal disease. Tooth sensitivity can become so uncomfortable that it may prevent a patient from eating or drinking certain foods, being outdoors in cold weather, or maintaining good oral hygiene practices. Tooth sensitivity is also a common complaint during dental bleaching regimens. Dental bleaching compositions, which typically comprise a peroxide bleaching agent, can cause tooth sensitivity and pain that, if left untreated, may cause the user to prematurely abort the bleaching process.

To relieve tooth sensitivity, there are currently many non-permanent treatment options available. The most common options include using desensitizing toothpastes, varnishes, gels, and rinses. These products may include, but are not limited to, desensitizing agents such as potassium nitrate, other potassium salts, citric acid, citrates, strontium chloride, stannous fluoride, and sodium fluoride.

Desensitizing dentifrices are a popular treatment option in treating sensitivity. To use desensitizing dentifrices, it is usually recommended that the patient use the dentifrice twice daily. However, results are not immediate. It usually takes an extended period of time (about 1–4 weeks) to be effective and to relieve sensitivity. The main reason for this is that people typically only brush their teeth for about 60 seconds or less, which translates into extremely limited contact time between the desensitizing agent and the person's teeth.

Another treatment involves the use of desensitizing gels that are applied using custom-fitted trays. The process of making a custom-fitted tray generally involves: (1) making an alginate impression of the patient's teeth; (2) making a stone cast or model of the impression; (3) vacuum forming a dental tray from the model, usually from a heated sheet of thin ethyl vinyl acetate (EVA) material, and (4) trimming to exclude gingival coverage. This method results in a tray that is soft and flexible, that is customized to very accurately fit over the patient's teeth, and that is therefore very comfortable to wear. In sum, the process for making a customized tray is time consuming, often taking days or weeks before the customized tray is available to the patient, and the resulting tray can be expensive.

Because of the time and cost associated with customized trays, less time consuming and costly alternatives have been developed. One alternative to customized dental trays is non-customized trays that approximate the shapes and sizes of a variety of users' dental arches. While non-customized dental trays can be used without the need for a professional customization procedure by a dentist, such trays tend to be more bulky and less comfortable than custom-fitted trays. Dental trays that can be self-customized (e.g., so-called "boil and bite" trays) are somewhat more comfortable and better-fitting compared to non-custom trays but less comfortable than trays that are customized by a dentist.

An alternative to the use of dental trays involves placing a flexible dental treatment strip over a user's tooth surfaces, typically for bleaching. Dental strips typically comprise a flexible plastic strip coated with a moist dental gel on the side of the strip facing the user's teeth. To install the strip, a portion of the strip is first placed over the front surfaces of the user's teeth, followed by folding the remainder of the strip around the occlusal edges of the teeth and back against a portion of the lingual surfaces. Like paint-on bleaching compositions, the use of dental strips does not require the user to use a customized or non-customized tray. An advantage of dental strips over paint-on compositions is that strips include a barrier that, at least in theory, protects the moist gel composition from diffusing into the user's mouth.

In reality, because of the generally poor adhesion of dental strips to the user's teeth, coupled with their generally flimsy nature, it is often difficult for the user to maintain the strips in their proper position. Dental strips are prone to slip off the teeth through even minimal movement of the user's mouth, jaw or tongue. Indeed, it is recommended that the user not eat, drink, smoke or sleep while wearing dental strips.

Even if a user successfully maintains the strip in its proper position during the entire treatment time, the flowable gel composition can diffuse into the person's saliva, potentially causing a poor taste in the user's mouth and possibly discomfort to soft oral and throat tissues. The tendency of the gel to diffuse into the user's mouth can be accelerated through even minimal shifts of the dental strip over the user's teeth, with each shift potentially exposing a new portion of the gel that remains adhered to the newly exposed surface of the user's teeth. In some cases, the dental strip can become so dislodged or mangled that it must be removed by the user and replaced with a fresh strip to complete the recommended treatment time. This multiplies the cost and hassle of the dental strip method.

In practical terms, the use of dental strips can greatly inhibit even the simplest of activities that involve movement of the user's mouth or tongue, such as talking, coughing, yawning, smiling, making other facial expressions, or even swallowing (which normally occurs subconsciously throughout the day). Indeed, the time when a person's mouth and tongue are prone to move the least is at night while the person is sleeping. Unfortunately, it is recommended that dental strips not be used while sleeping, presumably to prevent accidental choking on an inadvertently dislodged strip. This only confirms the tendency of conventional dental strips to easily dislodge from a user's teeth.

In view of the foregoing, there is an ongoing need for improved desensitizing compositions, apparatus and methods that are simple and easy to use, that more reliably remain in position over the user's teeth, and that result in less diffusion of desensitizing compositions into a user's oral cavity. Such improvements would be expected to improve or encourage compliance by the user.

BRIEF SUMMARY OF THE PREFFERED EMBODIMENTS

The present invention generally relates to shaped dental desensitizing compositions and devices used to desensitize a person's teeth, as well as methods for manufacturing and using such compositions and devices. Briefly summarized, the inventive dental desensitizing compositions are in a substantially solid form and shaped like a dental tray or in tray-like configuration. The substantially solid dental desensitizing compositions become more adhesive to teeth when moistened (e.g., by saliva or water). When placed over a person's teeth, the dental desensitizing compositions reliably adhere to the teeth, maintaining contact between the teeth to be treated and the desensitizing agent within the desensitizing composition.

In one embodiment, the shaped desensitizing composition is used in combination with a barrier layer that protects the desensitizing composition from ambient saliva or moisture found within the person's mouth. To the extent that a barrier layer is subsequently applied or attached to a shaped desensitizing composition, the shaped desensitizing composition may be considered to be an intermediate to a finished desensitizing device comprising the desensitizing composition and the barrier layer.

The optional barrier layer advantageously comprises a thin, flexible membrane formed from a moisture-resistant polymer material. Nevertheless, it is within the scope of the invention to provide barrier layers having any desired thickness or rigidity. In a preferred embodiment, the barrier layer comprises a thin layer of a polyolefin, polyester or similar moisture-resistant material. The barrier layer may comprise a conventional dental tray, examples of which include both customized and non-custom dental trays. The barrier layer may be as simple as a layer of a moisture resistant barrier forming material that is sprayed or painted on, applied by dipping, or otherwise applied to an existing desensitizing layer comprising a substantially solid dental desensitizing composition (e.g., one that is in the form of a dental tray or that otherwise has a desired shape).

The desensitizing composition is substantially solid and coherent, as opposed to a liquid, gel, paste, or dry particulate or powdery desensitizing composition. As such, the desensitizing composition comprises one or more coherent regions or masses of a dental desensitizing composition that do not readily run or flow. Providing a substantially solid and coherent desensitizing composition better adheres to a person's teeth and does not readily diffuse into the surrounding oral cavity on its own, absent becoming diluted by saliva or moisture in a person's mouth. This helps maintain the desensitizing composition between the optional barrier layer and the teeth being treated and helps prevent diffusion into the surrounding oral cavity. This, in turn, promotes better tooth desensitizing, patient compliance, and reduces the tendency of the user to taste the desensitizing composition when in use.

The substantially solid dental desensitizing compositions according to the invention include at least one dental desensitizing agent and at least one tooth adhesion agent. Preferred dental desensitizing agents include potassium nitrate. However, other non-limiting examples of dental desensitizing agents include other potassium salts, citric acid, citrates, strontium chloride, sodium fluoride, and stannous fluoride, although it is within the scope of the invention to use any dental desensitizing agents known in the art.

In one embodiment, the tooth adhesion agent advantageously remains substantially non-adhesive when the dental desensitizing composition is in a dry or substantially solid condition but becomes adhesive to teeth when the dental desensitizing composition is moistened, e.g., with water or saliva. A non-limiting example of a suitable tooth adhesion agent is polyvinyl pyrrolidone (PVP), although it is within the scope of the invention to use other tooth adhesion agents known in the art.

The dental desensitizing composition may include other components as desired to yield a final composition having desired properties. Examples of other components include, but are not limited to, plasticizers and humectants (e.g., glycerin, sorbitol, and polyethylene glycol), volatile solvents (e.g., water and alcohols), stabilizing agents (e.g., EDTA), neutralizing agents, thickening agents (e.g., fumed silica), bleaching agents (e.g., hydrogen peroxide), remineralizing agents (e.g., sodium fluoride or other fluoride salts), anti-microbial agents (e.g., chlorhexidine), antiplaque agents, anti-tartar agents, other medicaments, flavorants, sweeteners, and the like.

According to one embodiment, the dental desensitizing composition is made by first forming a flowable liquid or gel composition that is subsequently dried to form a substantially solid desensitizing layer. This may be performed by heating or otherwise causing one or more volatile solvents to be driven off by evaporation, thus leaving behind a substantially solid desensitizing composition. The drying process may be performed before or after the desensitizing composition is placed into contact with the barrier layer.

According to one embodiment, shaped dental desensitizing compositions according to the invention can be made by spreading a flowable dental desensitizing composition onto the surface of a large or continuous polymeric sheet. The polymeric sheet and desensitizing composition are then heated, such as in a forced air oven, to drive off a substantial portion of the water or other solvent that was used to form the flowable dental desensitizing composition in order to yield a substantially solid layer of desensitizing composition. Thereafter, individual tray-like dental desensitizing devices can be molded or stamped from the large or continuous polymeric sheet coated with the substantially solid layer of desensitizing composition and then separated as individual desensitizing devices suitable for placement over a person's teeth. Such desensitizing devices include a desensitizing layer comprising a shaped dental desensitizing composition according to the invention. Alternatively, the solid sheet of desensitizing composition can be separated from the polymer sheet and molded, stamped or otherwise formed into a desired shape.

Alternatively, a flowable or substantially solid dental desensitizing composition can be molded or shaped into a desired tray-like configuration comprising the desensitizing layer. Alternatively, the flowable composition can be cast onto a forming surface and dried to form a substantially solid sheet of desensitizing composition that is thereafter molded, stamped or otherwise formed into a desired shape. Thereafter, a barrier layer can be attached or applied to an outer surface of the desensitizing layer. In yet another embodiment, a dental tray can be coated with a flowable dental desensitizing composition, such as by painting or spreading, and then heated or allowed to dry at room temperature so that the desensitizing composition becomes substantially solid.

The size and shape of dental desensitizing compositions and desensitizing devices according to the invention can be tailored to more readily fit a person's upper or lower dental arch. They may also be tailored to fit persons having differently sized or shaped dental arches. The dental desensitizing compositions and devices are advantageously designed so as to substantially cover the front and lingual surfaces of the teeth to be desensitized. Desensitizing both surfaces helps in desensitizing the whole tooth, not just one side. The dental desensitizing devices are advantageously flexible and adhesive so as to readily conform to a wide variety of differently-sized teeth and dental arches.

The dental desensitizing compositions according to the invention are preferably in the shape of a dental tray having a front side wall, a rear side wall, and a trough between the front and rear side walls. Having the shape of a dental tray facilitates placement of the dental desensitizing composition or device over a person's teeth by minimizing the amount of manipulation that is necessary to obtain a good fit between the composition or device and the person's teeth. Dental desensitizing devices that are in the shape of a dental tray and that have a substantially solid desensitizing layer that becomes more adhesive when moistened with water or saliva are easier to install over a person's teeth than flat dental strips. In addition, the inventive dental desensitizing devices are designed to more reliably remain in place over the person's teeth compared to conventional dental strips. The result is more effective tooth desensitization and better patient compliance.

According to one embodiment, the dental desensitizing composition or device has a horseshoe shape and a U-shaped trough like a conventional desensitizing tray. In another embodiment, the desensitizing composition or device has an L-shaped profile or "trough". It will be appreciated, however, that dental desensitizing compositions or devices according to the invention can have any longitudinal profile or shape (e.g., they can be straight or have any desired degree of longitudinal curvature from one end of the device to the other). The trough may have any desired cross-sectional shape (e.g., the trough can be V-shaped, trapezoidal, rectangular, or other geometric shape).

To facilitate the ability of a dental treatment composition or device to conform to the various shapes and sizes among dental arches, the dental treatment composition or device may include mechanical features such as a notch within the front side wall, preferably within an edge near the center of the front side wall, and/or a notch within the rear side wall, preferably within an edge near the center of the rear side wall. Notches allow the tray-like desensitizing composition or device to more easily conform to differently-sized dental arches. In this way, the dental desensitizing composition or device can be designed so as to be "one-size fits all".

The dental desensitizing compositions, as well as desensitizing devices incorporating such compositions, can be designed to be worn for any desired time period. Increasing the concentration of dental desensitizing agent generally reduces the time it takes to desensitize teeth. Nevertheless, due to the extremely comfortable fit and reliable adhesion between the inventive dental desensitizing devices and the person's teeth, it is possible to wear such devices for extended periods of time in order to ensure even and thorough desensitization. Dental desensitizing compositions according to the invention can be designed to be worn while, e.g., talking, sleeping, eating, drinking, smiling, frowning, grimacing, yawning, coughing, smoking, or making virtually any facial expression or mouth contortion. This greatly decreases their intrusiveness into everyday activities compared to conventional dental strips, which do not reliably adhere to teeth, or intrusive treatment devices such as large, bulky dental appliances.

The dental desensitizing compositions, as well as devices incorporating such compositions, can be designed to be worn for as little as a few minutes or as long as several hours. By way of example and not limitation, such compositions usually require less time to be effective and can generally be worn for short durations (10–30 minutes), intermediate durations (30 minutes–2 hours), or long durations (2–12 hours) if needed. Desensitizing sessions may also be repeated as many times as are needed to obtain the desired degree of desensitization. The dental desensitizing compositions may be used in conjunction with dental bleaching compositions to decrease tooth sensitivity caused by bleaching, e.g., shaped solid dental bleaching compositions manufactured according to copending U.S. application Ser. No. 10/446,235, filed May 27, 2003, and U.S. application Ser. No. 10/446,741, filed May 27, 2003, previously incorporated by reference.

For convenience of use, multiple dental desensitizing compositions, as well as devices incorporating such compositions, may be packaged together and sold as a kit, either alone or in combination with the aforementioned solid dental bleaching compositions or other treatment devices. In one embodiment, the number of dental desensitizing compositions or devices provided with each kit can equal the number of sessions that represent a prescribed desensitizing regimen. To efficiently utilize the space within a kit package, multiple dental desensitizing compositions or devices can be stacked and interested together. The dental desensitizing compositions or devices can be sealed collectively or individually as desired. They may contain a removable protective layer on their interior surfaces to protect the desensitizing layer from contamination or moisture. It is within the scope of the invention to provide barrier layers and desensitizing composition that are initially separate and that are brought together by the end user. The desensitizing composition may be a dry or substantially solid insert or it may be a liquid or gel that is applied to the barrier and allowed to dry prior to placement of the finished dental treatment device over the person's teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
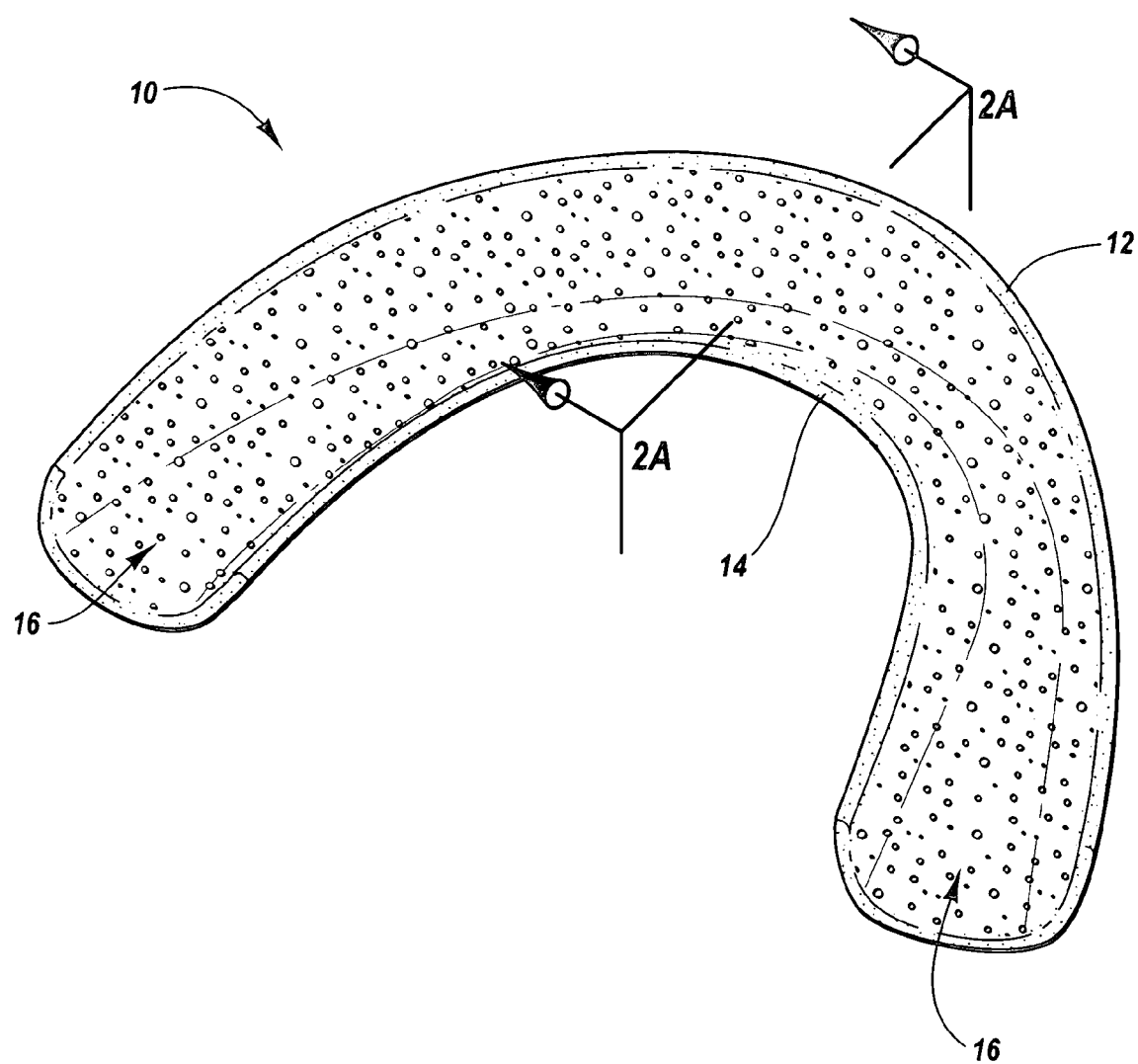
FIG. 1 is a perspective view of an exemplary dental desensitizing device according to the invention in the shape of a dental tray comprising a barrier layer and a substantially solid dental desensitizing composition.

The present invention generally relates to improved dental desensitizing compositions and devices used to desensitize a person's teeth, as well as methods for manufacturing and using such compositions and devices. The shaped dental desensitizing compositions are in a substantially solid form that becomes more adhesive to teeth when moistened with water or saliva. When placed over a person's teeth, the dental desensitizing composition reliably adheres to the teeth, maintaining contact between the teeth to be desensitized and the desensitizing agent within the desensitizing composition. A barrier layer may be provided that protects the dental desensitizing composition from diffusing away from the person's teeth as a result of ambient saliva or moisture found within the person's mouth.

The shaped desensitizing compositions are more adhesive to teeth than conventional dental strips. The inventive dental desensitizing devices are also less intrusive than bulky, over-the-counter, non-custom or boil and bite dental trays. In some ways they are as reliable as, or even more reliable than, custom-fitted dental trays in maintaining the dental desensitizing composition against a person's teeth. In some cases, they are also as comfortable, or even more comfortable, than custom-fitted trays.

The term "barrier layer", as used herein, refers to one or more layers of a moisture-resistant material that protects the desensitizing layer from ambient moisture and saliva found within a person's mouth when the dental desensitizing composition is placed over the person's teeth. The barrier layer may also serve to protect the desensitizing composition from moisture or other contaminants during storage and prior to use. The barrier layer may be in any desired form including, but not limited to, a sheet laminated to a surface of the desensitizing layer, a coating applied to a pre-formed desensitizing layer, or a dental treatment tray.

The term "shaped desensitizing composition", as used herein, refers to a dental desensitizing composition that has been formulated or processed so as to be substantially solid, coherent, and non-flowable. The term "desensitizing layer", as used herein, refers to one or more layers of a dental desensitizing composition that has been formulated or processed so as to be substantially solid, coherent, and non-flowable. The desensitizing layer may comprise a single continuous region or layer adjacent to the barrier layer, or it may comprise a plurality of discontinuous regions or layers spaced-apart by random or predetermined intervals.

The term "substantially solid", as used herein, refers to a dental desensitizing composition or layer that is in a solid or semi-solid condition so that it can be handled and placed against a person's teeth much like a dental tray. In one aspect, a "substantially solid" desensitizing composition or layer can be characterized as a continuous or cohesive mass that does not readily flow or separate when subjected to gravitational forces and which cannot be readily expressed through a syringe outlet or other similarly-sized opening or orifice. Thus, the term "substantially solid" excludes runny desensitizing liquids, viscous desensitizing liquids, and even thick desensitizing gels that are able to flow when subjected to gravity and/or which can be readily expressed through a syringe outlet or other similarly-sized opening or orifice. The term "substantially solid", when used in the context of a desensitizing composition or layer, excludes dry particulate desensitizing compositions or powders because dry particulates and powders readily flow when subjected to gravity and/or are readily separated (i.e., the particles as a whole have little or no internal cohesion). Moreover, powders or particulates, when viewed as a whole, are not "shaped", coherent, or solid. One characteristic of "substantially solid" desensitizing compositions or layers according to the invention is that they become more adhesive when an exposed surface thereof is moistened with, e.g., saliva or water. When moistened, the surface of the desensitizing composition or layer turns into a sticky material that is able to more strongly adhere to teeth compared to a substantially solid desensitizing composition or layer that has not been moistened. The composition at the surface may become a viscous liquid, paste or gel, at least temporarily, depending on the amount of moisture that is applied to the surface of the "substantially solid" desensitizing composition or layer. Nevertheless, the consistency of the moistened surface can remain "substantially solid" depending on the degree of initial moistening, or it can stiffen and even revert back to being "substantially solid" as the initial quantity of surface moisture diffuses into a remaining portion of the "substantially solid" desensitizing composition or layer over time (e.g., during a desensitizing procedure in which the desensitizing layer or composition is protected from saliva and ambient moisture in a person's mouth by a water-proof barrier layer).

The term "dental tray", as used herein, refers to any article of manufacture or device having a tray-like shape so as to facilitate placement of the device over at least a portion of a person's dental arch. A "dental tray" or "tray-like" device includes a front side wall configured to engage front surfaces of a person's teeth when in use, a rear side wall extending laterally from the front side wall, either abruptly by one or more distinct angles or non-abruptly by a curved transition, configured to engage lingual surfaces of the person's teeth, and a trough between said front and rear side walls. A "dental tray" may be configured so that a portion of the front side wall, rear side wall, or a transition portion thereof engages the incisal or occlusal edges of the person's teeth when in use. The dental tray may be curved or straight in the longitudinal dimension.

The term "trough", as used herein, refers to the region that is at least partially bounded by the front side wall, the rear side wall, and a plane or imaginary curved dome extending from an upper edge of the front side wall and an upper edge of the rear side wall. Thus, a "trough" can theoretically exist whenever the front and rear side walls have a space there between and are laterally offset by an angle of less than 180°. In practice, the front and rear side walls will be offset by an angle that is preferably less than about 150°, more preferably less than about 120°, and most preferably less than about 90°.

In the case of a trough having a U-shaped or rectangular cross section, at least a portion of the front and rear side walls may be substantially parallel (i.e., be offset by an angle of approximately 0°). In the case of a trough having a V-shaped or trapezoidal cross section, at least a portion of the front and rear side walls may be offset by an acute angle (i.e., by an angle between 0–90°). In the case of a trough having an L-shaped cross section, at least a portion of the front and rear side walls will be offset by an angle centered around approximately 90° (e.g., by an angle in a range of about 70° to about 110°). Thus, a trough having an L-shaped cross section can be a subset or slight variation of a trough having a V-shaped cross section.

The terms "longitudinal", "longitudinal dimension" and "longitudinal profile", as used herein when used to refer to a dental tray or dental treatment device, shall refer to the lengthwise dimension of the tray or device. The tray or device may be straight in the "longitudinal dimension" or it may be horseshoe-shaped or otherwise "longitudinally curved" in the longitudinal dimension so as to approximate the curvature of a person's dental arch, or at least facilitate placement of the tray or device over the dental arch.

The term "molecular weight", as used herein, refers to number average molecular expressed in Daltons unless otherwise specified.

II. Dental Desensitizing Compositions and Devices

The shaped dental desensitizing compositions can exist alone or in combination with a barrier layer as part of a dental desensitizing device. Such dental desensitizing devices typically include a shaped desensitizing composition or layer that becomes more adhesive to teeth when moistened by, e.g., saliva or water, and a moisture-resistant barrier layer that protects the desensitizing layer from ambient moisture within a person's mouth during use. Following are preferred examples of materials and characteristics of barrier layers and desensitizing compositions or layers according to the invention.

A. Barrier Layers

According to one embodiment of the invention, the barrier layer comprises a thin, flexible membrane formed from a moisture-resistant polymer material. In a preferred embodiment, the barrier layer comprises a thin, flexible layer of a polyolefin or similarly moisture-resistant material, such as wax, metal foil, paraffin, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes or polyesteramides. Such materials may be provided in the form of large, flat, flexible sheets to which the desensitizing composition or layer is applied. Alternatively, such sheets may be applied or attached to an existing desensitizing layer comprising a substantially solid dental desensitizing composition.

Notwithstanding the foregoing, it is within the scope of the invention to provide barrier layers having any desired material, thickness or rigidity so long as the barrier layer provides at least some moisture protection relative to the shaped desensitizing layer. The barrier layer may comprise a conventional dental tray, examples of which include both customized and non-custom dental trays. The barrier layer may be as simple as a layer of a moisture resistant material that is sprayed or painted on, applied by dipping, or otherwise applied to an existing desensitizing composition (e.g., one that is in the form of a dental tray or that otherwise has a desired shape).

Examples of suitable polyolefins for use in making the barrier layer include, but are not limited to, polyethylene (PE), high density polyethylene (HDPE), low density polyethylene (LDPE), ultra low density polyethylene (ULDPE), polypropylene, and polytetrafluoroethylene (PTFE) (e.g., TEFLON). An example of a suitable polyester for use in making the barrier layer includes, but is not limited to, polyethylene terephthalate (PET), an example of which is MYLAR, sold by DuPont. An example of a suitable polyurethane barrier material is a polyurethane film manufactured by Argotech. Plasticizers, flow additives, and fillers known in the art can be used as desired to modify the properties of any of the foregoing polymers used to form the barrier layer.

As will be discussed below, some dental desensitizing compositions will be more adhesive to polymer materials comprising the barrier layer than others, often depending on the tooth adhesion agent that is used. It has been found that, as between polyethylene, paraffin and polyethylene terephthalate, substantially solid dental desensitizing compositions tend to adhere more strongly to polyethylene terephthalate, particularly MYLAR.

It is also within the scope of the invention to utilize barrier layers that are formed onto a surface of a previously formed desensitizing composition, such by adhering a sheet or tray-like barrier layer to the desensitizing composition, which may then be thought of as a "desensitizing layer". Alternatively, the barrier layer may itself be initially flowable and later hardened, such as a lacquer that contains a barrier material (e.g., a cellulosic ether, cellulose acetate, wax, plastic, polyvinyl acetate, polyvinyl alcohol, or shellac) dissolved in one or more solvents that are later removed; a chemical or light-cure material (e.g., a methacrylate or acrylate resin); or a thermoplastic melt (e.g., any thermoplastic resin). Examples of useful cellulosic ethers that can be used to form a barrier layer include, but are not limited to, ethyl cellulose, propyl cellulose, isopropyl cellulose, butyl cellulose, t-butyl cellulose, and the like.

B. Substantially Solid Desensitizing Compositions and Layers

The substantially solid desensitizing compositions according to the invention can be in the shape of a dental tray, with or without a barrier layer. Where a barrier layer is present, the solid desensitizing composition may be thought of as a desensitizing layer. Prior to being moistened in preparation for or during use, desensitizing compositions or layers according to the invention preferably comprise a substantially solid and coherent dental desensitizing composition, as opposed to a liquid, a flowable gel, or a dry powder or particulate desensitizing composition. In the case of a desensitizing device, the desensitizing layer may comprise a single coherent mass or region, or it may comprise a plurality of coherent masses or regions of a substantially solid dental desensitizing composition adhered to the barrier layer. Providing a substantially solid and coherent desensitizing layer better maintains the desensitizing composition between the barrier layer and the teeth being desensitized instead of diffusing into the surrounding oral cavity, as compared to conventional desensitizing gels that are loaded into customized or non-customized dental trays. This, in turn, promotes better desensitization and patient compliance.

Substantially solid dental desensitizing compositions and layers according to the invention include at least one desensitizing agent and at least one tooth adhesion agent. In a preferred embodiment, the desensitizing agent is dispersed within a substantially solid matrix comprising the tooth adhesion agent. In one embodiment, the desensitizing agent may optionally be combined with a dental bleaching agent, such as hydrogen peroxide or a hydrogen peroxide complex, to form a bleaching composition that has decreased sensitivity. Following are preferred desensitizing, tooth adhesion, and bleaching agents.

1. Desensitizing Agents

A common dental desensitizing agent that is known to desensitize teeth and that has been found to be safe for oral use is potassium nitrate. Other desensitizing agents that can be used to desensitize teeth include, but are not limited to, other potassium salts, citric acid, citrates, strontium chloride, stannous fluoride, and sodium fluoride.

Desensitizing agents within the substantially solid dental desensitizing compositions according to the invention can have any desired concentration, e.g., between 0.01–50% by weight of the substantially solid dental desensitizing composition. The concentration of the dental desensitizing agent can be adjusted depending on the intended treatment time for each desensitizing session. In general, the shorter the treatment time, the more desensitizing agent will be added to accelerate dental desensitizing so as to effect desensitizing in a shorter time period.

In a preferred embodiment, potassium nitrate is the preferred desensitizing agent and is preferably included in an amount in a range of about 0.01 to about 50% by weight of the substantially solid dental desensitizing composition, more preferably in a range of about 0.05% to about 25% by weight of the substantially solid dental desensitizing composition, and most preferably in a range of about 0.1% to about 10% by weight of the substantially solid dental desensitizing composition.

Embodiments including other desensitizing agents instead of potassium nitrate, such as but not limited to, other potassium salts, citric acid, citrates, strontium chloride, sodium fluoride, and stannous fluoride, preferably include such agents in an amount in a range of about 0.1 to about 10% by weight of the substantially solid dental composition, and most preferably in a range of about 1–7% by weight of the substantially solid dental desensitizing composition.

In embodiments combining desensitizing agent potassium nitrate with a bleaching agent, such as but not limited to hydrogen peroxide, the desensitizing agent is preferably included in an amount in a range of about 0.01 to about 2% by weight of the substantially solid dental desensitizing composition, more preferably in a range of about 0.05% to about 1% by weight of the substantially solid dental desensitizing composition, and most preferably in a range of about 0.5% by weight of the substantially solid dental desensitizing composition. It has been found that including potassium nitrate within these ranges creates a synergistic effect with the dental bleaching agent that appears to enhance tooth whitening. It also provides the highest level of tooth desensitization when used with a bleaching agent.

2. Tooth Adhesion Agents

The tooth adhesion agent may comprise any known tackifying agent that is substantially non-adhesive, or less adhesive, when the dental desensitizing composition is substantially solid but which becomes more adhesive to teeth when the dental desensitizing composition is moistened with, e.g., water or saliva. A presently preferred tooth adhesion agent is polyvinyl pyrrolidone (PVP). PVP polymers have been found to provide excellent adhesion to polymer barrier layers made from PE, PET and paraffin, to be substantially non-adhesive when the dental desensitizing composition is dry to the touch, and to have superior adhesion to teeth when a surface of a substantially solid dental desensitizing composition is moistened with saliva or water.

Non-limiting examples of polyvinyl pyrrolidone polymers that may be useful in formulating desensitizing compositions and layers according to the invention include Kollidon 30, a polyvinyl pyrrolidone polymer sold by BASF having a molecular weight of 50,000, Kollidon VA 60, a polyvinyl pyrrolidone polymer having a molecular weight of 60,000, and Kollidon 90 F, a polyvinyl pyrrolidone polymer having a molecular weight of 1.3 million. Because PVP polymers having widely varying molecular weights have been found to provide similar adhesion and wetting properties, it is believed that PVP polymers of any molecular weight, at least those having a molecular weight between 50,000 and 1.3 million, will be useful in formulating substantially solid desensitizing compositions or layers according to the invention.

Other tooth adhesion agents that may be used in addition to, or instead of, PVP within the scope of the invention include, but are not limited to, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

Although polyethylene oxide polymers comprises a less preferred tooth adhesion agent, it has been found that a polyethylene oxide polymer having a molecular weight of 1 million provides better adhesion to barrier layers such as MYLAR than a polyethylene oxide polymer having a molecular weight of 100,000.

The one or more tooth adhesion agents are preferably included in an amount in a range of about 10% to about 90% by weight of the substantially solid dental desensitizing composition (exclusive of any bound water or other solvent), more preferably in a range of about 20% to about 80% by weight of the substantially solid dental desensitizing composition, and most preferably in a range of about 40% to about 75% by weight of the substantially solid dental desensitizing composition.

3. Other Components

The dental desensitizing compositions and layers may include other components as desired to yield a final composition or layer having desired properties. Examples of other components include, but are not limited to, plasticizers and humectants (e.g., glycerin, sorbitol, and polyethylene glycol), volatile solvents (e.g., water and alcohols, such as ethanol), stabilizing agents (e.g., EDTA), neutralizing agents (e.g., sodium hydroxide), thickening agents (e.g., fumed silica), bleaching agents (e.g. carbamide peroxide), remineralizing agents (e.g., sodium fluoride, stannous fluoride, sodium monofluorophosphate, and other fluoride salts), antimicrobial agents (e.g., chlorhexidine, troclosan, and tetracycline), antiplaque agents, anti-tartar agents (e.g., pyrophosphates salts), other medicaments, flavorants, sweeteners, and the like.

When water is used as a solvent when manufacturing desensitizing compositions or layers according to the invention and then driven off by evaporation to yield a substantially solid dental desensitizing composition, it is postulated that a significant amount of water remains bound or associated with the hydrophilic components within the dental desensitizing composition, including the dental desensitizing agent, the tooth adhesion agent, and any polyols added as humectants. Although the amount of residual water has not yet been determined, it is believed that approximately 10% of the water added initially remains after the initially flowable dental desensitizing composition is dried sufficiently to yield a substantially solid desensitizing composition.

Optional bleaching agents include, but are not limited to hydrogen peroxide, metal percarbonates, complexed hydrogen peroxides (e.g., carbamide peroxide or sodium perborate), chlorites, and hypochlorites, peroxy acids, and peroxy acid salts. When included, dental bleaching agents are preferably included in an amount in a range of about 5% to about 80% by weight of the dental desensitizing composition or layer, more preferably in a range of about 10% to about 60% by weight of the dental desensitizing composition or layer, and most preferably in a range of about 20% to about 50% by weight of the dental desensitizing composition or layer.

C. Characteristics of Dental Desensitizing Compositions and Desensitizing Devices Incorporating Such Compositions Dental desensitizing compositions according to the invention, as well as desensitizing devices incorporating such compositions, are preferably in the shape of a dental tray having a front side wall, a rear side wall, and a trough between the front and rear side walls. Having the shape of a dental tray facilitates placement of the dental desensitizing composition or device over a person's teeth by reducing the amount of manipulation that is necessary to obtain a good fit between the device and the person's teeth.

Dental desensitizing compositions and desensitizing devices in the shape of a dental tray that comprise a substantially solid shaped desensitizing composition that becomes more adhesive when moistened with water or saliva are easier to install over a person's teeth compared to dental strips or patches, which are initially flat and which must be manipulated so as to wrap the initially flat strip or patch around the occlusal or incisal edges of the teeth in order to cover the front and lingual tooth surfaces. In addition, the inventive dental desensitizing compositions and devices are designed to more reliably adhere and remain in place over the person's teeth compared to conventional dental strips, which employ a dental gel that is already flowable prior to placing the strip over a person's teeth to be treated. The result is more effective tooth desensitizing and better patient compliance. In contrast to conventional bleaching strips, which are not recommended for use while a person eats, drinks, smokes or sleeps, dental desensitizing compositions and devices according to the invention can be designed so as to be worn while talking, sleeping, eating, drinking, smiling, frowning, grimacing, yawning, coughing, smoking, or making virtually any facial expression or mouth contortion.

Figure 2A:
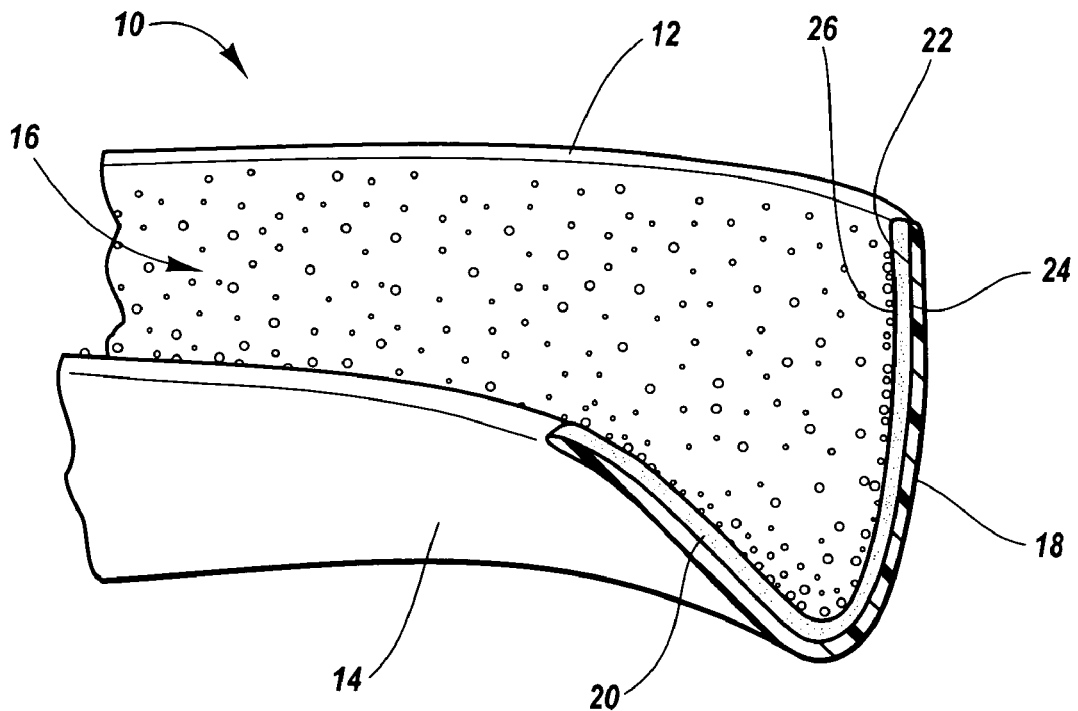
FIG. 2A is a cross-sectional view of the dental desensitizing device depicted in FIG. 1A.

According to one currently preferred embodiment, the dental desensitizing compositions and devices have a horseshoe shaped longitudinal profile and a trough with a U-shaped cross section, much like a conventional dental tray. An exemplary dental desensitizing device is depicted in FIGS. 1 and 2A. FIG. 1 is a perspective view of a dental desensitizing device 10 having a front side wall 12 and a rear side wall 14 that together have a generally horseshoe shape in a longitudinal dimension and that define a trough 16 having a generally U-shaped cross section. The U-shaped cross section of the trough is seen even more clearly in FIG. 2A.

The dental desensitizing device 10 further includes a barrier layer 18, preferably comprising a moisture-resistant material, and a coherent desensitizing layer 20, preferably comprising a substantially solid dental desensitizing composition. As best seen in FIG. 2A, the desensitizing layer 20 includes an exterior surface 22 disposed adjacent to an interior surface 24 of the barrier layer 18 and an interior desensitizing surface 26 designed to directly contact a person's teeth when the dental desensitizing device 10 is in use. An upper edge 28 of the barrier layer 18 can be designed so as to terminate at or shy of the gingival margin of a person's dental arch when in use.

Figure 2B:
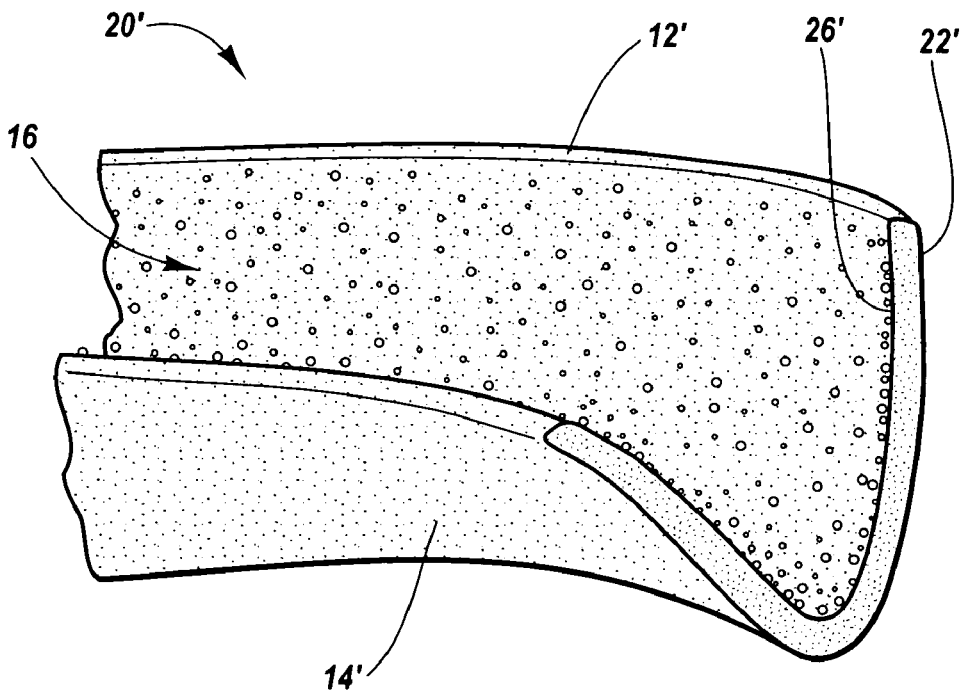
FIG. 2B is a cross-sectional view of an exemplary dental desensitizing composition according to the invention in the shape of a dental tray without a barrier layer.

FIG. 2B alternatively depicts a dental desensitizing composition 20' in the shape of a dental tray so as to have a front side wall 12' and a rear side wall 14' but with no barrier layer. The desensitizing composition 20' includes an interior desensitizing surface 26' designed to directly contact a person's teeth when the composition 20' is in use and an exterior surface 22' that may optionally be coated with a water-resistant barrier layer or material if desired to protect the desensitizing composition 20' from saliva (see FIG. 2A). The desensitizing composition 20' may be sold alone or together with a barrier layer or material.

Figure 3:
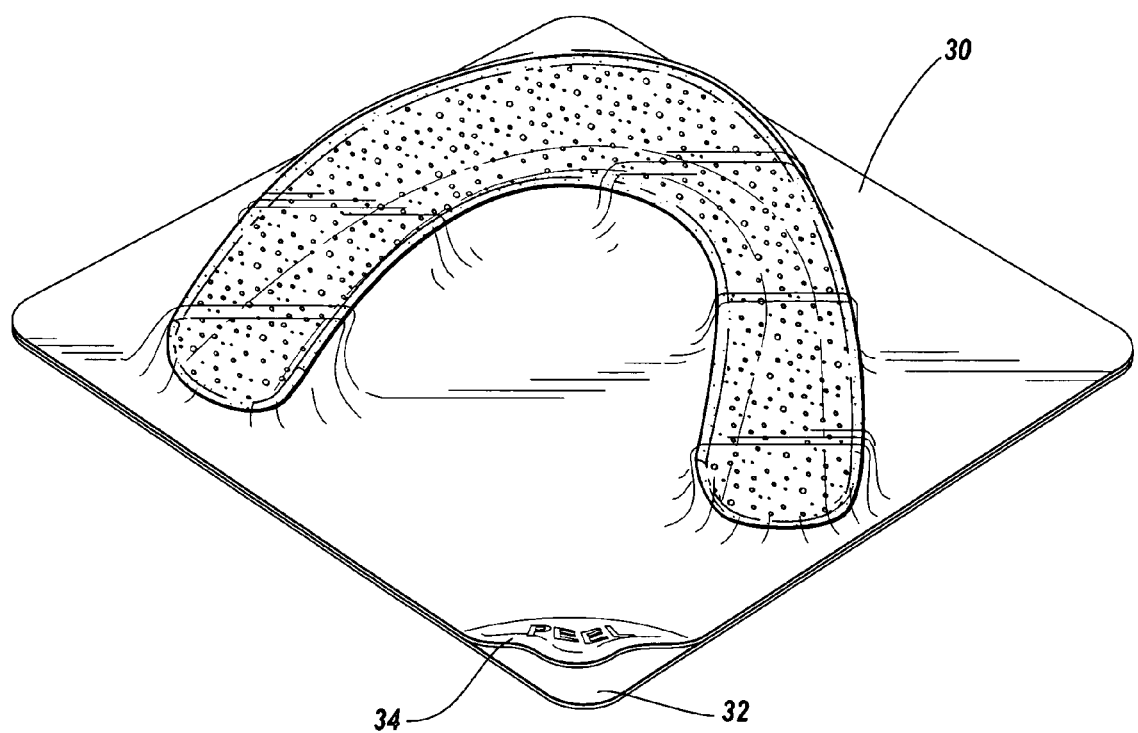
FIG. 3 illustrates a dental desensitizing device contained within a sealed protective package having a peelable cover.

In order to protect dental desensitizing compositions and devices according to the invention from contaminants during storage and prior to use, the dental desensitizing devices and compositions can be packaged within a sealed container or package. As illustrated in FIG. 3, the dental desensitizing device 10 can be sealed within a protective package 30 that includes a rigid support layer 32 and a peelable cover 34. When it is desired to use the dental desensitizing device 10, the peelable cover 34 is removed and the desensitizing device 10 is removed or separated from the support layer 32. In addition to, or instead of, the protective package 30, the dental desensitizing device 10 may alternatively include a removable protective layer (not shown) that is temporarily placed adjacent to the interior desensitizing surface 26 of the desensitizing layer 20. When it is desired to use the dental desensitizing device 10, the removable protective layer is removed so as to expose the interior desensitizing surface 20.

The protective package 30 or other protection means may also be used to protect shaped dental desensitizing compositions that do not include a barrier layer, such as the dental desensitizing composition 20' depicted in FIG. 2B.

Figure 4:
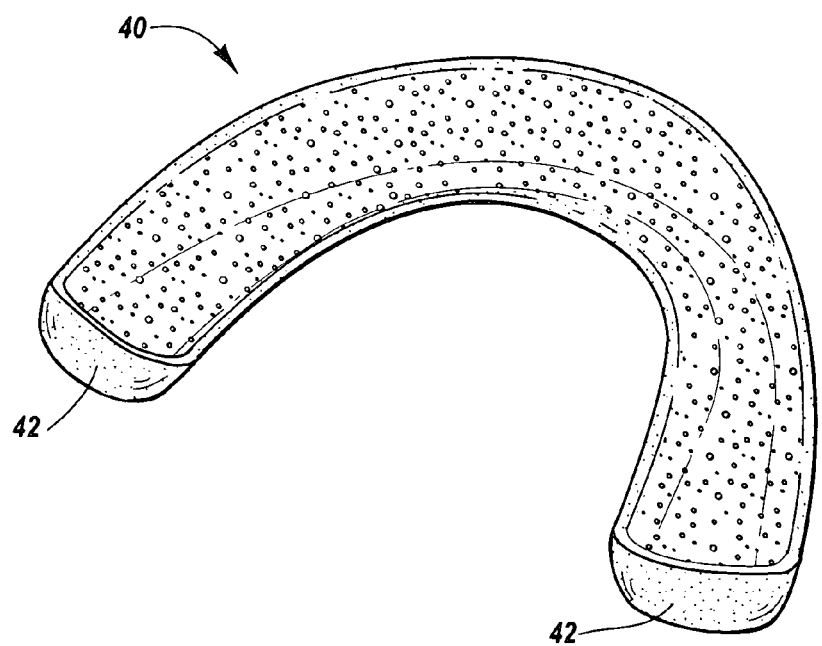
FIG. 4 is a perspective view of an exemplary dental desensitizing composition or device that is similar to the desensitizing device depicted in FIG. 1, or the desensitizing composition of FIG. 2B, but that further includes a terminal side wall on each longitudinal

FIG. 4 illustrates a dental desensitizing composition or device 40 that is a variation of the U-shaped dental desensitizing device 10 of FIGS. 1 and 2A or the desensitizing composition 20' shown in FIG. 2B. The main difference is that each longitudinal end 42 of the dental desensitizing composition or device 40 is raised so as to at least partially enclose the last tooth on each side of a person's dental arch when the desensitizing composition or device 40 is in use.

Figure 5:
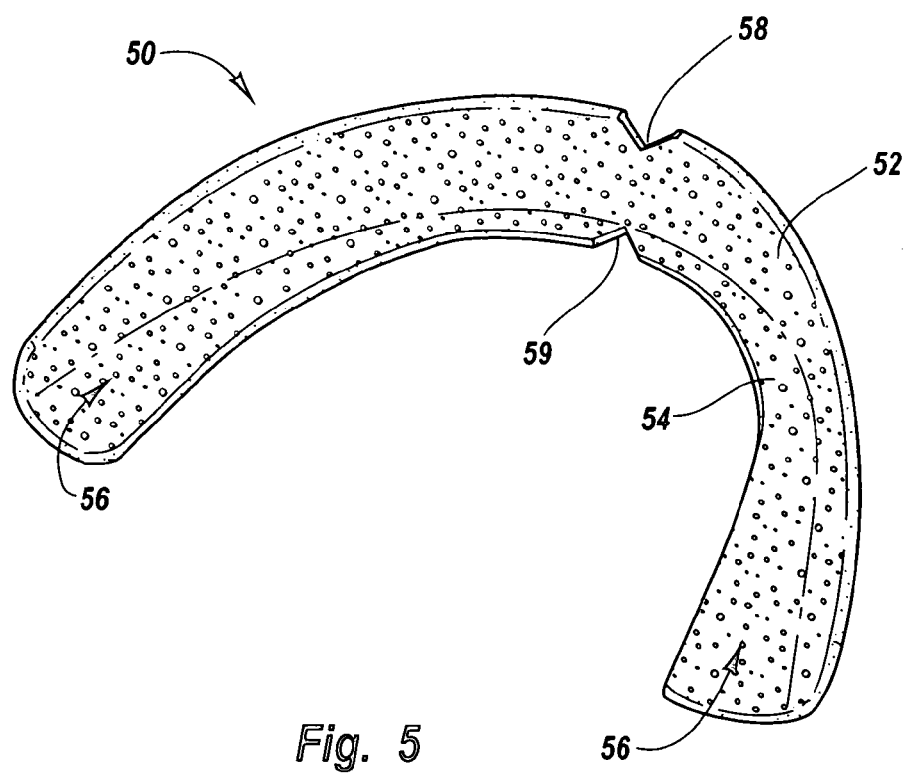
FIG. 5 is a perspective view of an exemplary dental desensitizing composition or device having an L-shaped trough and a curved longitudinal profile.

FIG. 5 illustrates an alternative embodiment of a dental desensitizing composition or device 50 according to the invention that is L-shaped. More particularly, the dental desensitizing composition or device 50 includes a front side wall 52 and a rear side wall 54 extending laterally from the front side wall 52 so as to form a trough 56 having an approximate L-shaped cross section. The L-shaped desensitizing composition or device 50 of FIG. 5 is somewhat easier to initially place over a person's dental arch compared to the U-shaped desensitizing compositions or devices of FIGS. 1–4. This is due to the approximately planar orientation of the rear side wall 54 relative to the occlusal or incisal edges of a person's teeth when the front side wall 52 of the dental desensitizing composition or device 50 is initially placed and adhered against the front surfaces of a person's teeth. On the other hand, more manipulation of an L-shaped desensitizing device is generally required to form and adhere the rear side wall 54 against the lingual surfaces of the person's teeth as a result of the greater initial offset angle between the front side wall 52 and rear side wall 54. However, the ability of dental desensitizing compositions and devices according to the invention to adhere to tooth surfaces almost immediately, or within a few seconds, after being wetted facilitates the process of conforming the front side wall 52 and rear side wall 54 to the person's tooth surfaces.

In the case of the dental desensitizing composition or device 50 having an L-shaped cross section, it may be more correct to say that the rear side wall 54 extending laterally from the front side wall 52 is really a bottom wall rather than a rear side wall. Nevertheless, because this erstwhile "bottom wall" of an L-shaped desensitizing composition or device is folded back against the lingual tooth surfaces during use, it can be readily seen that a desensitizing composition or device having an L-shaped trough is merely a variation of a composition or device having a V-shaped trough. Thus, for purposes of this disclosure and the appended claims, the side wall 54 shall constitute, and fall within the definition of, a "rear side wall".

To facilitate the ability of a dental desensitizing composition or device to conform to the varying shapes and sizes among dental arches, the composition or device may include mechanical features such as one or more notches within the front or rear side walls. As shown in FIG. 5, the dental desensitizing composition or device 50 includes a notch 58 in an outer edge near the center of the front side wall 52 and a notch 59 in an outer edge near the center of the rear side wall 54. Notches 58 and 59 allow the tray-like desensitizing composition or device to more easily spread open or compress when being conformed to differently-sized dental arches. In this way, the dental desensitizing composition or device 50 can more easily be a "one-size fits all" device.

Figure 6:
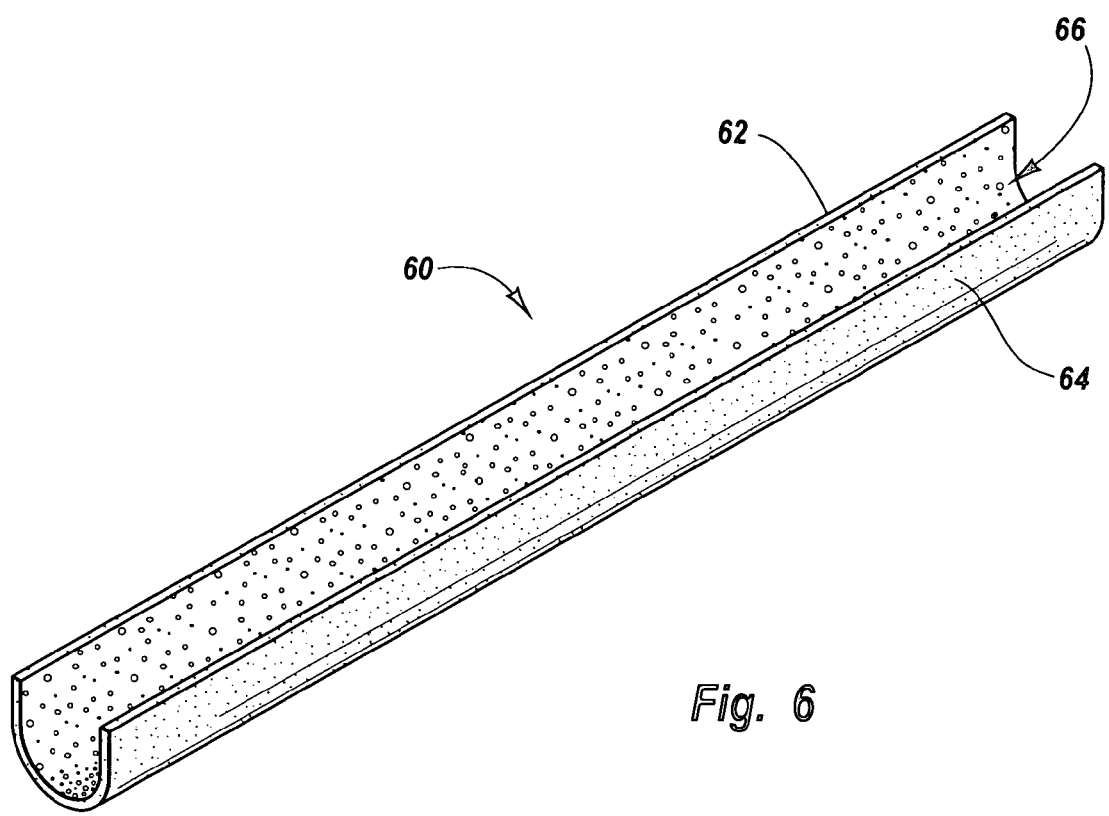
FIG. 6 is a perspective view of an exemplary dental desensitizing composition or device having a U-shaped trough and a substantially straight longitudinal profile.

FIG. 6 depicts an alternative embodiment of a dental desensitizing composition or device 60 according to the invention, which includes a front side wall 62 and a rear side wall 64 that define a U-shaped trough 66. Instead of being horseshoe shaped like the dental desensitizing compositions or device of FIGS. 1–5, or otherwise having a curved longitudinal profile, the dental desensitizing composition or device 60 of FIG. 6 has a substantially straight or linear longitudinal profile.

Figure 7:
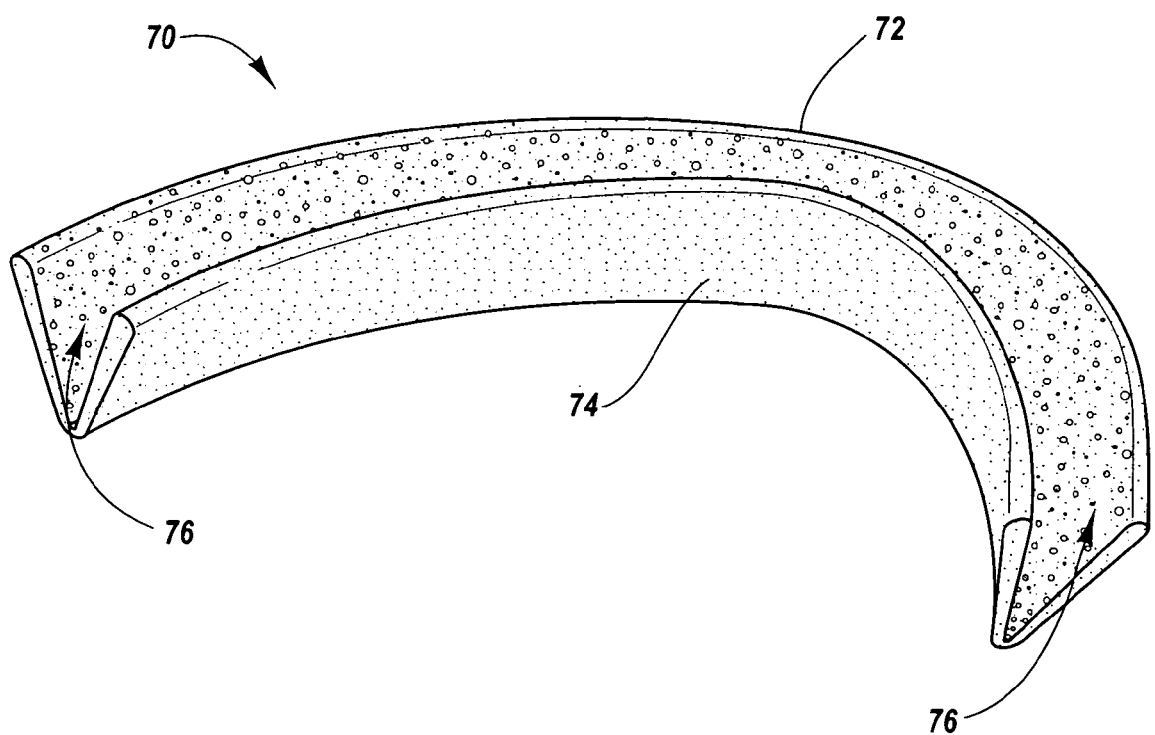
FIG. 7 is a perspective view of an exemplary dental desensitizing composition or device having a V-shaped trough and a curved longitudinal profile.

FIG. 7 depicts yet another alternative embodiment of a dental desensitizing composition or device 70 according to the invention. The dental desensitizing composition or device 70 includes a front side wall 72 and a rear side wall 74 that define a V-shaped trough 76 and a curved longitudinal profile. The main difference between the V-shaped desensitizing composition or device 70 of FIG. 7 and the L-shaped desensitizing composition or device 50 of FIG. 5 is the angle at which the front and rear side walls are laterally offset from each other.

Notwithstanding the foregoing examples, it will be appreciated that dental desensitizing compositions and devices according to the invention can have any longitudinal shape (e.g., they can have a straight or curved longitudinal profile from one end to the other). The front and rear side walls may define a trough of any desired cross-sectional shape (e.g., the trough can be trapezoidal, rectangular, or any other desired geometric shape).

The size and shape of dental desensitizing compositions according to the invention, as well as desensitizing devices incorporating such compositions, can be tailored to more readily fit either a person's upper dental arch or lower dental arch. They can be sized so as to desensitize all or merely a subset of a person's teeth. The dental desensitizing composition or device may be sufficiently adhesive and flexible so as to readily conform to a wide variety of differently-sized teeth and dental arches. The dental desensitizing compositions or devices are advantageously designed so as to substantially cover the front and lingual surfaces of the teeth to be desensitized. Desensitizing both surfaces yields a more even treatment, although it is certainly within the scope of the invention to desensitize one surface or more of one surface than another.

In general, the thickness of the barrier layer and/or the desensitizing composition within a desensitizing device can be adjusted to yield a dental desensitizing device having a desired strength and flexibility. In order for the barrier layer to remain flexible so as to conform to a person's teeth, the barrier layer will preferably have a thickness ranging from about 0.025 mm to about 1.5 mm.

The shaped desensitizing composition or layer will generally have a thickness ranging from about 0.1 mm to about 3 mm. The thickness of the desensitizing composition or layer can also be selected depending on the intended duration of each desensitizing session. In general, increasing the thickness of the desensitizing composition or layer will provide a longer or more sustained release of active dental desensitizing agent. By way of example, for short wear times, the desensitizing composition or layer will preferably have a thickness ranging from about 0.1 mm to about 0.5 mm. For intermediate wear times, the desensitizing composition or layer will preferably have a thickness ranging from about 0.5 mm to about 2 mm. For overnight treatments, the desensitizing composition or layer will preferably have a thickness ranging from about 2 mm to about 3 mm.

III. Method of Making Substantially Solid Dental Desensitizing Compositions and Desensitizing Devices Incorporating Such Compositions According to one embodiment, the dental desensitizing composition or layer is made by first forming a flowable desensitizing composition that is later dried to form a substantially solid desensitizing composition or layer. This may be performed by heating or otherwise causing one or more volatile solvents to be driven off by evaporation, thus leaving behind a substantially solid desensitizing composition or layer. The drying process may be performed before or after the desensitizing composition or layer is placed into contact with a barrier layer.

According to one embodiment, substantially solidified dental desensitizing compositions and desensitizing devices can be made by spreading a flowable dental desensitizing composition onto the surface of a large or continuous polymeric sheet (e.g., using a screeding device). The polymeric sheet and desensitizing composition are then placed into a forced air oven or other appropriate desiccation device in order to heat and drive off a substantial portion of the water or other solvent used to form the flowable dental desensitizing composition. Removal of the volatile solvent yields a desensitizing layer comprising a substantially solid desensitizing composition. Thereafter, individual tray-like dental desensitizing devices can be molded, such as by vacuum forming, pressing or stamping from the coated polymeric sheet and then separated into individual desensitizing devices suitable for placement over a person's teeth.

Alternatively, the substantially solid desensitizing composition can be separated from the polymeric sheet and then molded, stamped or otherwise formed into a desired shape of a dental desensitizing composition.

Alternatively, a flowable or substantially solid dental desensitizing composition can be molded or shaped into a desired tray-like configuration comprising the desensitizing composition or layer. Thereafter, a barrier layer may optionally be attached or applied to an outer surface of the shaped desensitizing composition or layer. In this embodiment, the barrier layer may comprise a solid polymeric sheet or other barrier material, or it may initially comprise a flowable barrier material or precursor that is later cured or hardened, such as by removing a solvent by evaporation, by chemical or light curing, or by cooling a thermoplastic melt.

In yet another embodiment of the invention, a barrier layer in the form of a dental tray or tray-like device (e.g., a customized or non-custom tray) can be coated with a flowable dental desensitizing composition. The desensitizing composition is then heated together with the dental tray or otherwise allowed to dry in order to form a shaped desensitizing layer comprising a substantially solid desensitizing composition. This process can be performed during commercial manufacture of the desensitizing device or by an end user.

IV. Methods of Using Dental Desensitizing Compositions and Devices Incorporating Such Compositions The dental desensitizing compositions according to the invention, as well as desensitizing devices incorporating such compositions, can be designed to be worn for any desired time period. Increasing the concentration of dental desensitizing agent generally reduces the desensitizing time required to effect desensitizing. Nevertheless, due to the extremely comfortable fit and reliable adhesion between the inventive dental desensitizing compositions or devices and the person's teeth, it is possible to wear such compositions or devices for extended periods of time in order to ensure more uniform desensitization. They may be designed to be worn while performing normal daily activities, such as talking, eating, drinking, smoking, coughing, smiling, frowning, grimacing, or while sleeping. This greatly decreases their intrusiveness into everyday activities compared to, e.g., conventional bleaching strips, which do not reliably adhere to teeth, or intrusive devices such as large, bulky dental appliances.

Dental desensitizing compositions or devices according to the invention may be worn over a person's upper dental arch, lower dental arch, or both simultaneously. The ability to reliably and comfortably wear dental desensitizing compositions or devices over the upper and lower dental arches simultaneously is another departure from bleaching strips, which are not recommended for use in the upper and lower dental arches at the same time.

Figure 8:
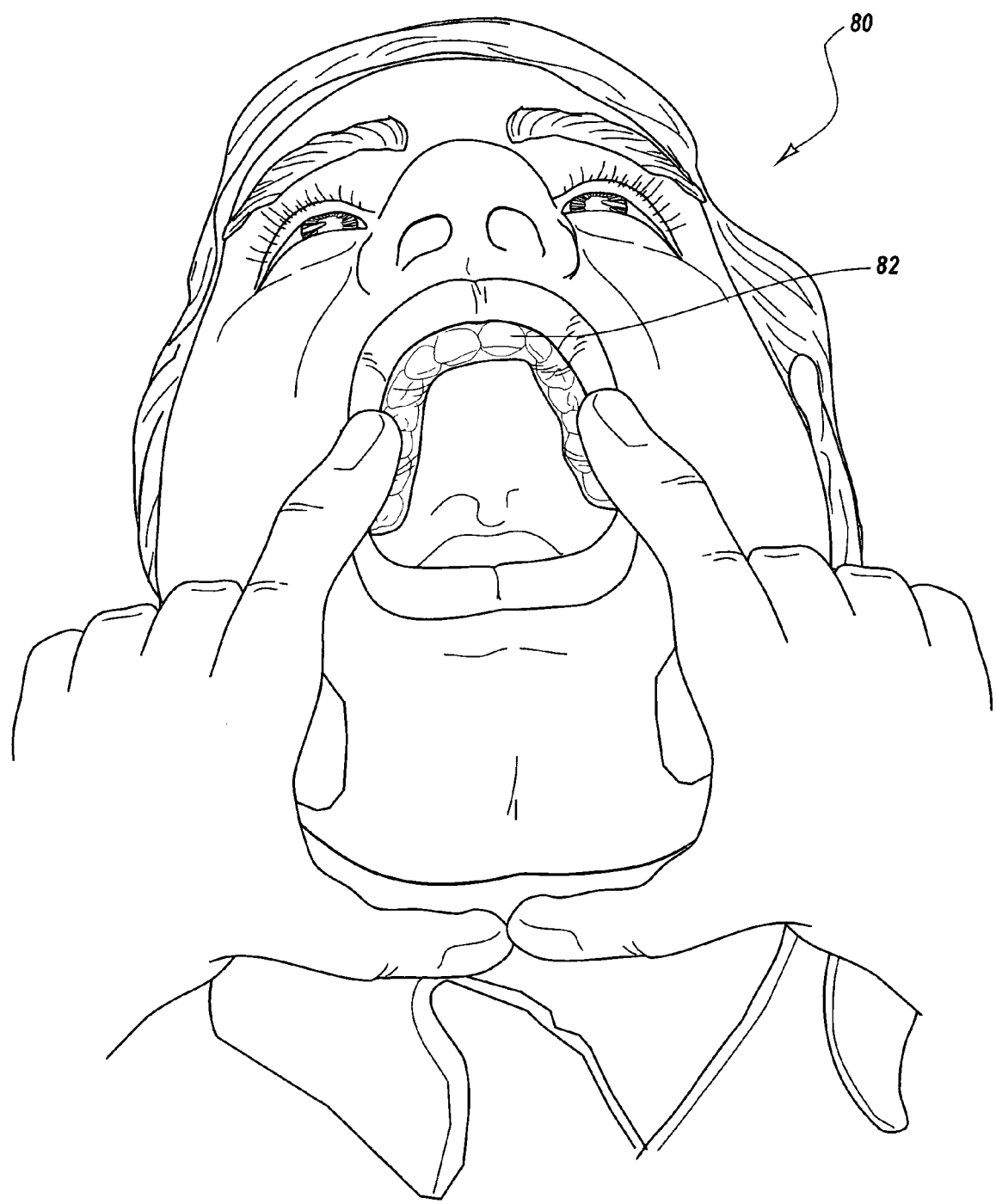
FIG. 8 illustrates a person placing a dental desensitizing composition or device according to the invention over the upper dental arch.
Figure 9:
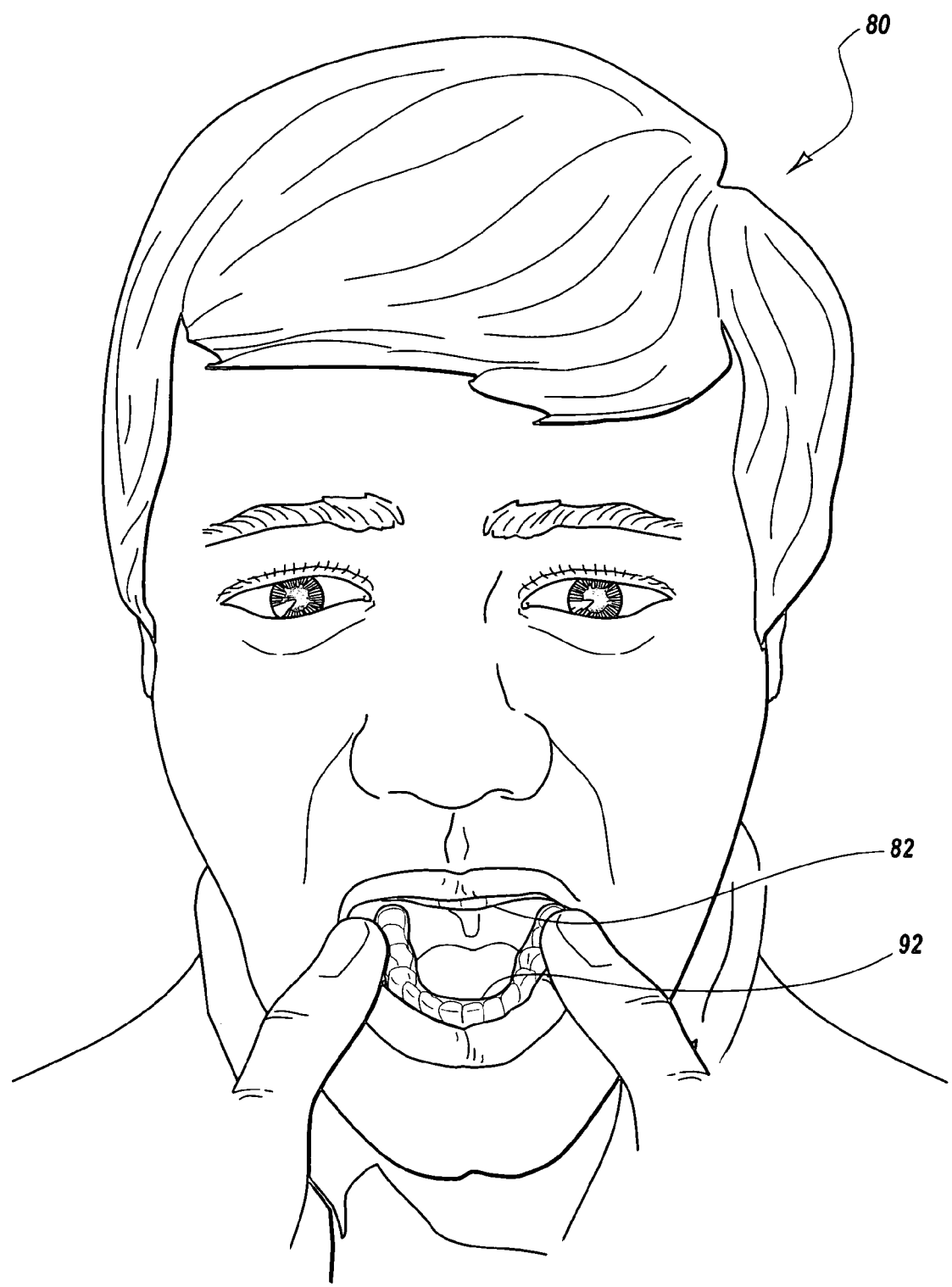
FIG. 9 illustrates a person placing a dental desensitizing composition or device according to the invention over the lower dental arch, with a dental desensitizing composition or device already placed over the upper dental arch.

FIG. 8 illustrates a person 80 placing a dental desensitizing composition or device 82 over the person's upper dental arch. FIG. 9 illustrates the person 80 placing a dental desensitizing composition or device 92 over the person's lower dental arch after having placed the dental desensitizing composition or device 82 over the upper dental arch. It will be appreciated, however, that the dental desensitizing compositions or devices can be placed over a person's upper and lower dental arches in any desired order.

To remove the desensitizing composition or device, a user can pry open a corner of the barrier layer or desensitizing composition using a fingernail or rigid tool and then pull the remainder off. Any residual desensitizing composition or layer that remains adhered to the person's teeth can be removed by washing or flushing water over the person's teeth, and/or by brushing. Although dental desensitizing compositions are very adhesive to teeth when protected from excessive moisture, they can be formulated to quickly break down and dissolve when flushed with excess water and/or by gentle mechanical action (e.g., brushing).

The dental desensitizing compositions or devices can be worn for as little as a few minutes and as long as several hours. By way of example, not limitation, a typical desensitizing session of short duration may last from about 10 to about 30 minutes. A desensitizing session of intermediate duration may last from about 30 minutes to about 2 hours. A desensitizing session of long duration, including overnight desensitizing while a person is sleeping, may last from about 2 hours to about 12 hours.

Desensitizing sessions may be repeated as many times as are needed to obtain a desired degree of desensitization. In some cases, a clinical effect has been observed after only 1–3 desensitizing sessions. A typical desensitizing regimen will preferably include 1–20 desensitizing sessions, more preferably 2–15 desensitizing sessions, and most preferably 3–10 desensitizing sessions.

The dental desensitizing devices or compositions according to the invention may be used in conjunction with a dental bleaching regimen. In such a case, the inventive dental devices or compositions may be used preliminarily to applying a dental bleaching composition, subsequent to applying a dental bleaching composition, or simultaneous with applying a dental bleaching composition. The dental bleaching composition may be in the form of a gel (e.g., that is placed into a custom or non-custom tray), a bleaching strip (e.g., that is coated with a bleaching gel), or a substantially solid bleaching composition in the shape of a tray or tray-like device. Examples of suitable bleaching compositions in the form of a tray or tray-like shape are disclosed in copending U.S. application Ser. Nos. 10/446,235 and 10/446,741, both of which were filed May 27, 2003 and which were previously incorporated by reference.

V. Dental Desensitizing Kits

For convenience of use, multiple dental desensitizing compositions or devices may be packaged together and sold as a kit. In one embodiment, the number of dental desensitizing compositions or devices provided with each kit will equal the number of sessions that represent a prescribed desensitizing regimen. Because of the ease of placing the inventive dental desensitizing compositions or devices over a person's teeth, coupled with the reliability with which they achieve adhesion to teeth, the likelihood that a particular desensitizing composition or device will not work as intended or fail is greatly decreased compared to conventional strips.

To efficiently utilize the space within a kit package, multiple dental desensitizing compositions or devices can be stacked or interested together. The dental desensitizing compositions or devices can be sealed collectively or individually as desired. A protective package 30 is depicted in FIG. 3. The desensitizing composition or layer may optionally contain a removable protective layer on an interior surface to protect the desensitizing composition or layer from contamination or moisture.

It is within the scope of the invention to provide barrier layers and shaped desensitizing compositions that are initially separate and that are brought together by the end user. For example, the shaped desensitizing compositions may be a substantially solid insert that is placed into a customized or non-custom tray, that is coated with an initial flowable barrier material, or that is covered with a flexible barrier sheet. Alternatively, a flowable dental desensitizing composition can be placed within the trough of a tray-like barrier layer and allowed to solidify so as to yield a shaped dental desensitizing composition or layer.

The dental desensitizing devices or compositions according to the invention may be used in conjunction with a dental bleaching regimen. In such a case, it may be desirable to provide a kit that includes one or more dental desensitizing compositions or devices and one or more dental bleaching compositions or devices. The dental bleaching composition may be in the form of a gel (e.g., that is placed into a custom or non-custom tray), a bleaching strip (e.g., that is coated with a bleaching gel), or a substantially solid bleaching composition or device in the shape of a tray or tray-like device. Examples of suitable bleaching compositions and devices in the form of a tray or tray-like shape are disclosed in copending U.S. application Ser. Nos. 10/446,235 and 10/446,741, both of which were filed May 27, 2003 and which were previously incorporated by reference.

VI. Examples of the Preferred Embodiments

The following are several examples of dental desensitizing compositions that have been formulated and manufactured according to the invention. Such exemplary formulations and manufacturing conditions are given by way of example, and not by limitation, in order to illustrate dental desensitizing compositions that have been found to be useful for desensitizing a person's teeth. Unless otherwise indicated, all percentages are by weight.

Example 1

An initially flowable dental desensitizing composition suitable for use in manufacturing a substantially solid, cohesive, and non-flowable dental desensitizing composition was formed by mixing together the following components:

| | |
|---|---|
| Sodium Flouride | 0.25% |
| Polyvinyl pyrrolidone (M.W. = 1.3 million) | 30% |
| Water | 69.75% |

The resulting desensitizing composition was spread over the surfaces of three types of flexible polymer sheets: polyethylene sheets having a thickness of approximately 0.15 to 0.18 mm; sheets made of paraffin having a thickness of approximately 0.05 to 0.08 mm; and MYLAR sheets having a thickness of approximately 0.38 mm. The desensitizing composition was spread using a screeding device. The coated sheets were heated in a forced air oven heated to a temperature of 50–70° C. for approximately 1 hour. The coated sheets were removed from the oven and inspected. The desensitizing composition had dried sufficiently so as to form a solid, coherent layer of desensitizing layer on the surface of the polymer sheets. The dried desensitizing composition adhered well to each of the polymer sheets.

The coated sheets were removed from the oven a second time, cut apart into smaller-sized pieces, and shaped into tray-like dental desensitizing devices suitable for placement over a person's teeth. The tray-like desensitizing devices included front and rear side walls that defined a trough having an approximate U- or V-shaped cross section and were curved in the longitudinal dimension to roughly approximate the curvature of a dental arch.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

Example 2

An initially flowable dental desensitizing composition suitable for use in manufacturing a substantially solid, cohesive, and non-flowable dental desensitizing composition was formed by mixing together the following components:

| | |
|---|---|
| Sodium Citrate | 5% |
| Polyvinyl pyrrolidone (M.W. = 1.3 million) | 20% |
| Water | 75% |

The resulting desensitizing composition was manufactured into desensitizing devices according to the method described in Example 1. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

Example 3

An initially flowable dental desensitizing composition suitable for use in manufacturing a substantially solid, cohesive, and non-flowable dental desensitizing composition was formed by mixing together the following components:

| | |
|---|---|
| Potassium Nitrate | 3% |
| Polyvinyl pyrrolidone (M.W. = 1.3 million) | 15% |
| Ethanol | 30% |
| Water | 52% |

The resulting desensitizing composition was manufactured into desensitizing devices according to the method described in Example 1. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

Example 4

An initially flowable dental desensitizing composition suitable for use in manufacturing a substantially solid, cohesive, and non-flowable dental desensitizing composition was formed by mixing together the following components:

| | |
|---|---|
| Potassium Nitrate | 0.5% |
| Sodium Flouride | 0.25% |
| Polyvinyl pyrrolidone (M.W. = 1.3 million) | 32% |
| Ethanol | 30% |
| Water | 37.25% |

The resulting desensitizing composition was manufactured into desensitizing devices according to the method described in Example 1. The dried desensitizing composition adhered well to the barrier layers comprising polymer sheets.

The tray-like dental desensitizing devices were tested by placing them over a person's teeth. The residual saliva present on the tooth surfaces moistened the exposed surface of the dry dental desensitizing composition and caused it to become sticky and very adhesive to teeth almost immediately. The desensitizing devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable desensitizing was detected after 1–3 desensitizing sessions.

Example 5

An initially flowable desensitizing bleaching composition suitable for use in manufacturing a substantially solid, cohesive, and non-flowable desensitizing bleaching composition was formed by mixing together the following components:

| | |
|---|---|
| Potassium Nitrate | 0.5% |
| Sodium Flouride | 0.25% |
| Carbamide Peroxide | 15% |
| Polyvinyl pyrrolidone (M.W. = 1.3 million) | 33% |
| Water | 51.25% |

The resulting desensitizing composition was manufactured into desensitizing devices according to the method described in Example 1. The dried desensitizing composition adhered well to the barrier layers comprising polymer sheets.

The tray-like desensitizing bleaching devices were tested by placing them over a person's teeth. The residual saliva present on the tooth surfaces moistened the exposed surface of the dry dental desensitizing composition and caused it to become sticky and very adhesive to teeth almost immediately. The desensitizing bleaching devices were pressed against the teeth, which caused them to conform to the natural irregularities of the dental arch and adhere firmly against the teeth.

The tray-like dental desensitizing devices were worn for varying time periods ranging from several minutes to several hours without becoming dislodged. In some cases a noticeable desensitizing effect was detected after just one desensitizing session (e.g., a 2-hour desensitizing session). In all cases, noticeable bleaching was detected after 1–3 desensitizing sessions.

The following hypothetical examples are given in order to more fully define the invention. While these examples are hypothetical in nature, they are based on actual mix designs that have been made and tested.

Example 6

An initially flowable dental desensitizing composition suitable for use in manufacturing a substantially solid, cohesive, and non-flowable dental desensitizing composition is formed by mixing together the following components:

| | |
|---|---|
| Desensitizing Agent | 16% |
| Polyvinyl pyrrolidone (M.W. = 1.3 million) | 38% |
| Water | 46% |

The desensitizing agent may be any known desensitizing agent, including those disclosed herein. The resulting desensitizing composition is manufactured into desensitizing devices according to the method described in Example 1. The dried desensitizing composition adheres well to the barrier layers comprising polymer sheets. The desensitizing devices can be used to desensitize a person's teeth.

Example 7

An initially flowable dental desensitizing composition suitable for use in manufacturing a substantially solid, cohesive, and non-flowable dental desensitizing composition is formed by mixing together the following components:

| | |
|---|---|
| Desensitizing Agent | 16% |
| PolyOx WSR 101 (M.W. = 1 million) | 7% |
| Water | 77% |

The desensitizing agent may be any known desensitizing agent, including those disclosed herein. The resulting desensitizing composition is manufactured into desensitizing devices according to the method described in Example 1. The dried desensitizing composition does not adhere strongly to the polymer sheets but is easily separated from the sheets. The desensitizing devices can be used to desensitize a person's teeth. Thus, while polyethylene oxide is a satisfactory teeth adhesion agent, it is less satisfactory in promoting adhesion between a dried dental desensitizing composition and a polymer sheet.

Example 8

An initially flowable dental desensitizing composition suitable for use in manufacturing a substantially solid, cohesive, and non-flowable dental desensitizing composition is formed by mixing together the following components:

| | |
|---|---|
| Desensitizing Agent | 16% |
| Carbopol 974P | 5% |
| Aqueous NaOH (50%) | 6% |
| Water | 73% |

The desensitizing agent may be any known desensitizing agent, including those disclosed herein. The resulting desensitizing composition is manufactured into desensitizing devices according to the method described in Example 1. Although the desensitizing composition is able to dry sufficiently to form a solid, it tends to shrink due to the large amount of water needed to cause Carbopol to form a gel. The desensitizing devices can be used to desensitize a person's teeth, although they do not adhere as readily to a person's teeth compared to compositions that use PVP or polyethylene oxide.

Example 9

An initially flowable dental desensitizing composition suitable for use in manufacturing a substantially solid, cohesive, and non-flowable dental desensitizing composition is formed by mixing together the following components:

| | |
|---|---|
| Polyethylene Oxide (M.W. = 100,000) | 20% |
| Glycerin | 2.5% |
| Desensitizing Agent | 2.4% |
| Water | 75.1% |

The desensitizing agent may be any known desensitizing agent, including those disclosed herein. The resulting desensitizing composition is manufactured into desensitizing devices according to the method described in Example 1. The dried desensitizing composition does not adhere strongly to the polymer sheets but is easily separated from the sheets. The desensitizing devices can be used to desensitize a person's teeth. Thus, while polyethylene oxide is a satisfactory teeth adhesion agent, it is less satisfactory in promoting adhesion between a dried dental desensitizing composition and a polymer sheet.

Example 10

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Water | 25% |
| Ethanol | 25% |
| Polyvinyl pyrrolidone (M.W. = 1.3 million) | 38% |
| Glycerin | 73% |

The desensitizing agent may be any known desensitizing agent, including those disclosed herein. The resulting desensitizing composition is manufactured into desensitizing devices according to the method described in Example 1. Using a mixture of water and ethanol as the solvent allows the desensitizing composition to dry in less than time than the compositions that use water as the only solvent. The inclusion of glycerin helps the desensitizing composition remain more flexible and less brittle after drying. The dried desensitizing composition adheres well to the barrier layers comprising polymer sheets. The desensitizing devices can be used to desensitize a person's teeth.

Example 11

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Water | 21% |
| Ethanol | 21% |
| Kollidon VA 64 (M.W. = 60,000) | 40% |
| Carboxy methyl cellulose | 3% |
| PEG 600 | 5% |

Kollidon VA 64 is a polyvinyl pyrrolidone polymer sold by BASF. The desensitizing agent may be any known desensitizing agent, including those disclosed herein. The resulting desensitizing composition is manufactured into desensitizing devices according to the method described in Example 1. Using a mixture of water and ethanol as the solvent allows the desensitizing composition to dry in less than time than the compositions that use water as the only solvent. The inclusion of PEG helps the desensitizing composition remain more flexible and less brittle after drying. The dried desensitizing composition adheres well to the barrier layers comprising polymer sheets. The desensitizing devices can be used to desensitize a person's teeth.

Example 12

An initially flowable dental desensitizing composition suitable for use in manufacturing a substantially solid, cohesive, and non-flowable dental desensitizing composition is formed by mixing together the following components:

| | |
|---|---|
| Desensitizing Agent | 11.6% |
| Ethanol | 55.8% |
| Kollidon VA 90 F (M.W. = 1.3 million) | 24.4% |
| Carboxy methyl cellulose | 2.3% |
| PEG 600 | 5.8% |

The desensitizing agent may be any known desensitizing agent, including those disclosed herein. The resulting desensitizing composition is manufactured into desensitizing devices according to the method described in Example 1. Using ethanol as the only solvent allows the desensitizing composition to dry in even less time than compositions that use a mixture of water and ethanol as the only solvent. The inclusion of PEG helps the desensitizing composition remain more flexible and less brittle after drying. The dried desensitizing composition adheres well to the barrier layers comprising polymer sheets. The desensitizing devices can be used to desensitize a person's teeth.

Example 13

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Ethanol | 65% |
| Kollidon VA 90 F (M.W. = 1.3 million) | 20% |
| PEG 600 | 5% |

The desensitizing agent may be any known desensitizing agent, including those disclosed herein. The resulting desensitizing composition is manufactured into desensitizing devices according to the method described in Example 1. Using ethanol as the only solvent allows the desensitizing composition to dry in even less time than compositions that use a mixture of water and ethanol as the only solvent. The inclusion of PEG helps the desensitizing composition remain more flexible and less brittle after drying. The dried desensitizing composition adheres well to the barrier layers comprising polymer sheets. The desensitizing devices can be used to desensitize a person's teeth.

Example 14

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Ethanol | 64% |
| Kollidon VA 90 F (M.W. = 1.3 million) | 25% |
| PEG 600 | 1% |

The desensitizing agent may be any known desensitizing agent, including those disclosed herein. The resulting desensitizing composition is manufactured into desensitizing devices according to the method described in Example 1. Using ethanol as the only solvent allows the desensitizing composition to dry in even less time than compositions that use a mixture of water and ethanol as the only solvent. The inclusion of PEG helps the desensitizing composition remain more flexible and less brittle after drying. The dried desensitizing composition adheres well to the barrier layers comprising polymer sheets. The desensitizing devices can be used to desensitize a person's teeth.

Example 15

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Ethanol | 64% |
| Kollidon VA 90 F (M.W. = 1.3 million) | 23% |
| PEG 600 | 1% |
| Aerosil 200 | 2% |

The desensitizing agent may be any known desensitizing agent, including those disclosed herein. The resulting desensitizing composition is manufactured into desensitizing devices according to the method described in Example 1. Using ethanol as the only solvent allows the desensitizing composition to dry in even less time than compositions that use a mixture of water and ethanol as the only solvent. The inclusion of PEG helps the desensitizing composition remain more flexible and less brittle after drying. Aerosil 200 is added as a tackifying agent to promote adhesion of the wet desensitizing composition to the polymer sheets. The dried desensitizing composition adheres well to the barrier layers comprising polymer sheets. The desensitizing devices can be used to desensitize a person's teeth.

Example 16

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Ethanol | 66.9% |
| Kollidon VA 90 F (M.W. = 1.3 million) | 20% |
| PEG 600 | 0.1% |
| Aerosil 200 | 3% |

The desensitizing agent may be any known desensitizing agent, including those disclosed herein. The resulting desensitizing composition is manufactured into desensitizing devices according to the method described in Example 1. Using ethanol as the only solvent allows the desensitizing composition to dry in even less time than compositions that use a mixture of water and ethanol as the only solvent. Aerosil 200 is added as a tackifying agent to promote adhesion of the wet desensitizing composition to the polymer sheets. The dried desensitizing composition adheres well to the barrier layers comprising polymer sheets. The desensitizing devices can be used to desensitize a person's teeth.

Example 17

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| PolyOx (M.W. = 1 million) | 7.5% |
| Water | 75.5% |
| Glycerin | 5% |
| Aerosil 200 | 2% |

The desensitizing agent may be any known desensitizing agent, including those disclosed herein. The resulting desensitizing composition is manufactured into desensitizing devices according to the method described in Example 1. The inclusion of glycerin helps the desensitizing composition remain more flexible and less brittle after drying. The desensitizing composition does not adhere well to MYLAR sheets. It also shrinks somewhat after extended drying. The desensitizing devices can be used to desensitize a person's teeth.

Example 18

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Kollidon 90 F (M.W. = 1.3 million) | 10% |
| Kollidon 30 (M.W. = 50,000) | 20% |
| Water | 53% |
| Glycerin | 5% |
| Aerosil 200 | 2% |

The desensitizing agent may be any known desensitizing agent, including those disclosed herein. The resulting desensitizing composition is manufactured into desensitizing devices according to the method described in Example 1. The inclusion of glycerin helps the desensitizing composition remain more flexible and less brittle after drying. Aerosil 200 is added as a tackifying agent to promote adhesion of the wet desensitizing composition to the polymer sheets. The dried desensitizing composition adheres well to each of the polymer sheets. The desensitizing devices can be used to desensitize a person's teeth.

Example 19

An initially flowable dental desensitizing composition suitable for use in manufacturing a substantially solid, cohesive, and non-flowable dental desensitizing composition was formed by mixing together the following components:

| | |
|---|---|
| Desensitizing Agent | 10% |
| Kollidon 90 F (M.W. = 1.3 million) | 27% |
| Water | 50% |
| Glycerin | 7% |
| Aerosil 200 | 6% |

The desensitizing agent may be any known desensitizing agent, including those disclosed herein. The resulting desensitizing composition is manufactured into desensitizing devices according to the method described in Example 1. The inclusion of glycerin helps the desensitizing composition remain more flexible and less brittle after drying. Aerosil 200 is added as a tackifying agent to promote adhesion of the wet desensitizing composition to the polymer sheets. The dried desensitizing composition adheres well to each of the polymer sheets. The desensitizing devices can be used to desensitize a person's teeth.

Example 20

An initially flowable dental desensitizing composition suitable for use in manufacturing a substantially solid, cohesive, and non-flowable dental desensitizing composition is formed by mixing together the following components:

| | |
|---|---|
| Desensitizing Agent | 10% |
| Kollidon 90 F (M.W. = 1.3 million) | 28% |
| Water | 50% |
| Glycerin | 7% |
| Aerosil 200 | 5% |

The desensitizing agent may be any known desensitizing agent, including those disclosed herein. The resulting desensitizing composition is manufactured into desensitizing devices according to the method described in Example 1. The inclusion of glycerin helps the desensitizing composition remain more flexible and less brittle after drying. Aerosil 200 is added as a tackifying agent to promote adhesion of the wet desensitizing composition to the polymer sheets. The dried desensitizing composition adheres well to each of the polymer sheets. The desensitizing devices can be used to desensitize a person's teeth.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An article of manufacture for use in desensitizing a person's teeth, comprising:
a substantially solid and coherent dental desensitizing composition having a tray-like configuration comprising a front side wall, a rear side wall, and a trough between said front and rear side walls,
said dental desensitizing composition having a rigidity so as to maintain itself in the tray-like configuration absent external support,
said desensitizing composition having increased adhesiveness to teeth when moistened by saliva or water,
said desensitizing composition comprising:
at least one dental desensitizing agent; and
at least one tooth adhesion agent that forms a substantially solid matrix within which said dental desensitizing agent is dispersed and that at least partially contributes to said increased adhesiveness to teeth when said dental desensitizing composition is moistened by saliva or water.

2. An article of manufacture as defined in claim 1, said desensitizing composition being initially horseshoe shaped prior to use so that said desensitizing composition at least approximately conforms to a person's dental arch with minimal longitudinal shaping.

3. An article of manufacture as defined in claim 1, said desensitizing composition initially having a longitudinal curvature that is less than the curvature of a person's dental arch prior to use so that additional longitudinal curving of said desensitizing composition is required when said desensitizing composition is plated over a person's teeth.

4. An article of manufacture as defined in claim 1, said desensitizing composition initially having a substantially straight longitudinal profile prior to use so that longitudinal curving of said desensitizing composition is required when said desensitizing composition is placed over a person's teeth.

5. An article of manufacture as defined in claim 1, at least a portion of said trough having an approximate U-shaped cross section.

6. An article of manufacture as defined in claim 1, at least a portion of said trough having an approximate V-shaped cross section.

7. An article of manufacture as defined in claim 1, at least a portion of said trough having an approximate L-shaped cross section.

8. An article of manufacture as defined in claim 1, at least a portion of said trough having approximately a rectangular or trapezoidal cross section.

9. An article of manufacture as defined in claim 1, said dental desensitizing agent comprising at least one of potassium nitrate, potassium salt, citric acid, citrate, strontium chloride, sodium fluoride, or stannous fluoride.

10. An article of manufacture as defined in claim 1, said dental desensitizing agent having a concentration in a range of about 0.01% to about 50% by weight of said desensitizing composition.

11. An article of manufacture as defined in claim 1, said dental desensitizing agent having a concentration in a range of about 0.5% to about 25% by weight of said desensitizing composition.

12. An article of manufacture as defined in claim 1, said dental desensitizing agent having a concentration in a range of about 0.1% to about 10% by weight of said desensitizing composition.

13. An article of manufacture as defined in claim 1, said tooth adhesion agent comprising polyvinyl pyrrolidone.

14. An article of manufacture as defined in claim 1, said tooth adhesion agent comprising at least one of carboxypolymethylene, polyethylene oxide, polyacrylic acid, copolymer of polyacrylic acid, polyacrylate, polyacrylamide, copolymer of polyacrylic acid and polyacrylamide, PVP-vinyl acetate copolymer, carboxymethylcellulose, carboxypropylcellulose, polysaccharide gum, or protein.

15. An article of manufacture as defined in claim 1, said tooth adhesion agent having a concentration in a range of about 10% to about 90% by weight of said desensitizing composition.

16. An article of manufacture as defined in claim 1, said tooth adhesion agent having a conceptration in a range of about 20% to about 80% by weight of said desensitizing composition.

17. An article of manufacture as defined in claim 1, said tooth adhesion agent having a concentration in a range of about 40% to about 75% by weight of said desensitizing composition.

18. An article of manufacture as defined in claim 1, said desensitizing composition further comprising at least one humectant.

19. An article of manufacture as defined in claim 1, wherein said desensitizing composition is sized and configured so as to fit over at least a portion of a person's upper dental arch.

20. An article of manufacture as defined in claim 1, wherein said desensitizing composition is sized and configured so as to fit over at least a portion of a person's lower dental arch.

21. An article of manufacture as defined in claim 1, wherein said desensitizing composition has a cross-sectional thickness in a range of about 0.1 mm to about 0.5 mm.

22. An article of manufacture as defined in claim 1, wherein said desensitizing composition has a cross-sectional thickness in a range of about 0.5 mm to about 2 mm.

23. An article of manufacture as defined in claim 1, wherein said desensitizing composition has a cross-sectional thickness in a range of about 2 mm to about 3 mm.

24. An article of manufacture as defined in claim 1, wherein said desensitizing composition is sized and configured so as to approximately terminate at or near a person's gingival margin when said denial desensitizing composition is in use.

25. An article of manufacture as defined in claim 1, wherein said desensitizing composition is contained within a sealed package prior to use.

26. An article of manufacture as defined in claim 1, further comprising a barrier layer comprising a moisture-resistant material adjacent to an outer surface of said desensitizing composition that protects the desensitizing composition firm saliva or moisture when in use.

27. An article of manufacture as defined in claim 26, said barrier layer being flexible so that it will readily conform to the shape of a person's teeth when in use.

28. An article of manufacture as defined in claim 26, said barrier layer comprising at least one polyolefin.

29. An article of manufacture as defined in claim 28, said polyolefin comprising at least one of polyethylene, high density polyethylene, low density polyethylene, ultra-low density polyethylene, polypropylene, or polytetrafluoroethylene.

30. An article of manufacture as defined in claim 26, said barrier layer comprising at least one of wax, metal foil, paraffin, ethylene-vinyl acetate copolymer, ethylene-vinyl alcohol copolymer, polycaprolactone, polyester, polycarbonate, polyurethane, polyatnide, or polyesteramide.

31. An article of manufacture as defined in claim 1, said desensitizing composition further comprising at least one dental bleaching agent.

32. An article of manufacture as defined in claim 31, said dental bleaching agent having a concentration in a range of about 5% to about 80% by weight of said desensitizing composition.

33. An article of manufacture as defined in claim 31, said dental bleaching agent having a concentration in a range of about 10% to about 60% by weight of said desensitizing composition.

34. An article of manufacture as defined in claim 31, said dental bleaching agent having a concentration in a range of about 20% to about 50% by weight of said desensitizing composition.

35. A kit for use in desensitizing a person's teeth comprising a plurality of substantially solid desensitizing compositions having a tray-like configuration according to claim 1.

36. An article of manufacture comprising a dental desensitization device for use in desensitizing a person's teeth, said dental desensitization device comprising:
a barrier layer comprising a moisture-resistant material in the shape of a dental tray comprising a front side wall, a rear side wall, and a trough between said front and rear side walls; and
a desensitizing layer within said trough comprising a substantially solid dental desensitizing composition having a first surface adjacent to said barrier layer and a second surface that has increased adhesiveness to teeth when moistened by saliva or water, said desensitizing layer being in the shape of a dental tray and having a rigidity so as to at least partially contribute to maintaining said dental desensitizing device in the shape of a dental tray prior to placing said desensitizing device aver a person's teeth said desensitizing composition comprising:
at least one dental desensitizing agent; and
at least one tooth adhesion agent that forms a substantially solid matrix within which said dental desensitizing agent is dispersed and that at least partially contributes to said increased adhesiveness to teeth when said dental desensitizing composition is moistened by saliva or water.

37. An article of manufacture as defined in claim 36, at least a portion of said trough having a cross section that is approximately U-shaped, V-shaped, L-shaped, rectangular, or trapezoidal.

38. An article of manufacture as defined in claim 36, said barrier layer being flexible so that it will readily conform to the shape of a person's teeth when in use.

39. An article of manufacture as defined in claim 36, said barrier layer comprising at least one polyolefin.

40. An article or manufacture as defined in claim 39, said polyolefin comprising at least one of polyethylene, high density polyethylene, low density polyethylene, ultra-low density polyethylene, polypropylene, or polytetrafluoroethylene.

41. An article of manufacture as defined in claim 36, said barrier layer comprising at least one of wax, metal foil, paraffin, ethylene-vinyl acetate copolymer, ethylene-vinyl alcohol copolymer, polycaprolactone, polyester, polycarbonate, polyurethane, polyamide, or polyesteramide.

42. An article of manufacture as defined in claim 36, said barrier layer having a rigidity so as to at least partially contribute to maintaining said dental desensitizing device in the shape of a dental tray prior to placing said desensitizing device over a person's teeth.

43. An article of manufacture as defined in claim 36, said barrier layer being initially horseshoe shaped prior to use so that said dental desensitizing device at least approximately conforms to a person's dental arch with minimal longitudinal shaping.

44. An article of manufacture as defined in claim 36, said barrier layer initially having a longitudinal curvature that is less than the curvature of a person's dental arch prior to use so that additional longitudinal curving of said dental desensitizing device is required when said dental desensitizing device is placed over a person's teeth.

45. An article of manufacture as defined in claim 36, said barrier layer initially having a substantially straight longitudinal profile prior to use so that longitudinal curving of said dental desensitizing device is required when said dental desensitizing device is placed over a person's teeth.

46. An article of manufacture as defined in claim 36, said barrier layer comprising a customized dental tray.

47. An article of manufacture as defined in claim 36, said desensitizing layer comprising a single coherent mass in the shape of a dental tray comprising a front side wall, a rear side wall, and a trough between said front and roar side walls.

48. An article of manufactured as defined in claim 36, said dental desensitizing agent comprising at least one member selected from potassium nitrate, other potassium salts, citric acid, citrates, strontium chloride, sodium fluoride, or stannous fluoride.

49. An article of manufacture as defined in claim 36, at least a portion of said tooth adhesion agent comprising polyvinyl pyrrolidone.

50. An article of manufacture as defined in claim 36, said desensitizing composition further comprising at least one dental bleaching agent.

51. A kit fix use in desensitizing a person's teeth comprising a plurality of dental desensitizing devices according to claim 36.

52. A method for desensitizing a person's teeth comprising obtaining a dental desensitizing device according to claim 36 and then placing said dental desensitizing device over at least a portion of the person's teeth for a desired time period.

53. A method of manufacturing an article of manufacture comprising a substantially solid and coherent dental desensitizing composition, the method comprising:
mixing together a dental desensitizing agent, a tooth adhesion agent and a solvent to form an intermediate flowable composition; and
removing at least a portion of said solvent from said intermediate flowable composition so as to form said substantially solid and coherent dental desensitizing composition,
said dental desensitizing composition having a tray-like configuration comprising a front side wall, a rear side wall, and a trough between said front and rear side walls.

54. A method or manufacturing an article of manufacture as defined in claim 53, further comprising forming a barrier layer adjacent to said dental desensitizing composition.

55. A method of manufacturing an article of manufacture as defined in claim 54, wherein said barrier layer comprises a dental tray.

56. A method of manufacturing an article of manufacture as defined in claim 55, said method comprising first placing said intermediate flowable composition adjacent to said dental tray prior and then removing at least a portion of said solvent from said intermediate flowable composition to form said substantially solid and coherent dental desensitizing composition.

57. A method of manufacturing an article or manufacture as defined in claim 55, said method comprising first forming said dental desensitizing composition having a tray-like configuration and then placing it inside a trough within said dental tray.

58. A method of manufacturing an article of manufacture as defined in claim 54, said method comprising applying an initially flowable material adjacent to said denial desensitizing composition and allowing the initially flowable material to substantially solidify into a solid barrier layer.

59. A method of manufacturing an article of manufacture as define in claim 54, said method comprising first placing said intermediate flowable composition adjacent to a polymeric sheet comprising said barrier layer, removing at least a portion of said solvent from said intermediate flowable composition to form a substantially solid and coherent dental desensitizing composition, and shaping said dental desensitizing composition and barrier layer into the tray-like configuration.

60. A method of manufacturing art article of manufacture as defined in claim 54, wherein said barrier layer comprises a single layer of a water-resistant polymeric material.

* * * * *

UNITED STATES PATENT AND TRADEMARK OFFICE
CERTIFICATE OF CORRECTION

| | |
|---|---|
| PATENT NO. | : 7,059,857 B2 |
| APPLICATION NO. | : 10/637237 |
| DATED | : June 13, 2006 |
| INVENTOR(S) | : Allred et al. |

It is certified that error appears in the above-identified patent and that said Letters Patent is hereby corrected as shown below:

<u>TITLE Page ITEM (65), Related U.S. Application Data</u>
Line 3, after "application No." please delete "10/446,741" and insert --10/446,471--

<u>Column 7</u>
Line 10, after "longitudinal" please insert --end;--

<u>Column 11</u>
Line 56, after "substantially" please delete "sold" and insert --solid--

<u>Column 30</u>
Line 19, after "having a" please delete "conceptration" and insert --concentration--
Line 49, after "when said" please delete "denial" and insert --dental--
Line 56, after "composition" please delete "firm" and insert --from--

<u>Column 31</u>
Line 8, after "polyurethane," please delete "polyatnide," and insert --polyamide--
Line 44, after "device" please delete "aver" and insert --over--
Line 44, after "teeth" please insert --,--

<u>Column 32</u>
Line 32, after "front and" please delete "roar" and insert --rear--
Line 34, after "article of" please delete "manufactured" and insert --manufacture--
Line 45, after "kit" please delete "fix" and insert --for--

UNITED STATES PATENT AND TRADEMARK OFFICE
CERTIFICATE OF CORRECTION

PATENT NO. : 7,059,857 B2
APPLICATION NO. : 10/637237
DATED : June 13, 2006
INVENTOR(S) : Allred et al.

It is certified that error appears in the above-identified patent and that said Letters Patent is hereby corrected as shown below:

<u>Column 34</u>
Line 1, after "to said" please delete "denial" and insert --dental--
Line 13, after "manufacturing" please delete "art" and insert --an--

Signed and Sealed this

Fifth Day of December, 2006

JON W. DUDAS
*Director of the United States Patent and Trademark Office*